United States Patent [19]

Krapcho

[11] 4,316,905
[45] Feb. 23, 1982

[54] MERCAPTOACYL DERIVATIVES OF VARIOUS 4-SUBSTITUTED PROLINES

[75] Inventor: John Krapcho, Somerset, N.J.

[73] Assignee: E. R. Squibb & Sons, Inc., Princeton, N.J.

[21] Appl. No.: 164,985

[22] Filed: Jul. 1, 1980

[51] Int. Cl.³ ............... A61K 31/40; C07D 207/12
[52] U.S. Cl. .................. 424/274; 424/263;
424/246; 424/250; 424/251; 260/326.2;
260/326.25; 260/326.36; 260/326.43; 546/256;
546/281; 260/326.35; 424/240; 260/326.22;
260/326.47

[58] Field of Search ........... 260/326.2, 326.25, 326.22,
260/326.35, 326.47, 326.36, 326.43; 546/281,
256; 424/263, 274

[56] References Cited

U.S. PATENT DOCUMENTS

| | | | |
|---|---|---|---|
| 3,485,819 | 12/1969 | Weisenborn et al. | 260/239.1 |
| 3,946,000 | 3/1976 | Naito et al. | 260/243 C |
| 4,046,889 | 9/1977 | Ondetti et al. | 260/326.2 |
| 4,105,776 | 8/1978 | Ondetti et al. | 260/326.2 |
| 4,116,962 | 9/1978 | Ondetti et al. | 260/326.25 |
| 4,154,935 | 5/1979 | Ondetti et al. | 260/326.2 |

FOREIGN PATENT DOCUMENTS

| | | | |
|---|---|---|---|
| 2028327 | 8/1978 | United Kingdom | 260/326.2 |
| 2027025 | 2/1980 | United Kingdom | 260/326.2 |

OTHER PUBLICATIONS

Mauger et al. Chem. Rev. vol. 66. p. 47–86 1966.

*Primary Examiner*—Jane T. Fan
*Attorney, Agent, or Firm*—Lawrence S. Levinson; Stephen B. Davis

[57] ABSTRACT

This invention is directed to compounds of the formula

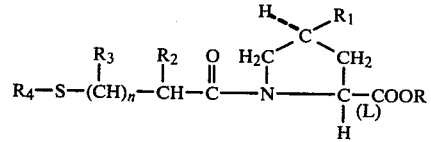

and various intermediates therefore. The final products possess useful hypotensive activity.

37 Claims, No Drawings

MERCAPTOACYL DERIVATIVES OF VARIOUS 4-SUBSTITUTED PROLINES

BACKGROUND OF THE INVENTION

Ondetti et al. in U.S. Pat. No. 4,105,776 disclose that various mercaptoacyl prolines or substituted prolines, for example, where the proline ring is substituted in the 4-position by a hydroxy or lower alkyl group are useful as hypotensive agents due to their angiotensin converting enzyme inhibition activity.

Mercaptoacyl derivatives of proline wherein the acyl sidechain can be substituted by an alkyl or trifluoromethyl group and the proline can be substituted with one or more halogens are disclosed as useful hypotensive agents by Ondetti et al. in U.S. Pat. No. 4,154,935.

Mercaptoacyl derivatives of proline wherein the acyl sidechain can be substituted with a lower alkylthio group are also disclosed as useful hypotensive agents by Ondetti et al. in U.S. Pat. No. 4,116,962.

Mercaptoacyl derivatives of proline wherein the proline ring is substituted in the 3- or 4-position by an ether or thioether group are disclosed as useful hypotensive agents by Ondetti et al. in U.S. Pat. No. 126,239 filed Mar. 3, 1980.

Mercaptoacyl derivatives of 4-disubstituted prolines and 4-substituted dehydroprolines are disclosed as useful hypotensive agents by Krapcho in U.S. Ser. No. 86,905 filed Oct. 22, 1979.

Mercaptoacyl derivatives of proline substituted in the 5-position by various groups such as phenyl, hydroxyphenyl, cycloalkyl, aralkyl, etc., are disclosed as useful hypotensive agents by Iwao et al. in U.K. Patent Application No. 2,027,025.

SUMMARY OF THE INVENTION

This invention is directed to new mercaptoacyl derivatives of various 4-cis substituted prolines of formula I and salts thereof

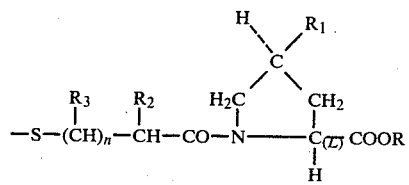
(I)

R represents hydrogen or lower alkyl.

$R_1$ represents $-(CH_2)_m$-cycloalkyl, 1-cyclohexenyl, 1,4-cyclohexadienyl,

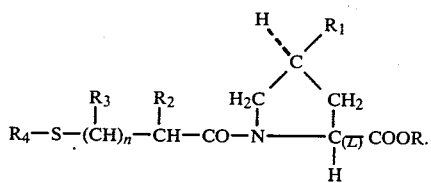

$-(CH_2)_m-(\alpha$-naphthyl), $-(CH_2)_m-(\beta$-naphthyl), $-(CH_2)_m-$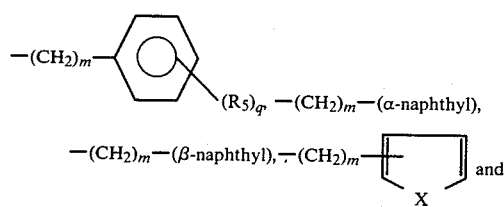 and $-(CH_2)_m-$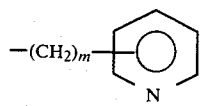.

$R_2$ and $R_3$ are independently selected from hydrogen, lower alkyl, lower alkylthio and halo substituted lower alkyl.

n is zero, one or two.

$R_4$ is hydrogen, a hydrolyzably removable protecting group, a chemically removable protecting group, or m is zero, one, two or three.

$R_5$ is hydrogen, lower alkyl of 1 to 4 carbons, especially methyl, lower alkoxy of 1 to 4 carbons, especially methoxy, lower alkylthio of 1 to 4 carbons, especially methylthio, chloro, bromo, fluoro, trifluoromethyl, hydroxy, phenyl, phenoxy, phenylthio, or phenylmethyl. The hydroxy substituted compounds are obtained by heating the corresponding methoxy substituted compound with pyridine HCl.

q is one, two or three provided that q is more than one only if $R_5$ is hydrogen, methyl, methoxy, chloro or fluoro.

X is oxygen or sulfur.

DETAILED DESCRIPTION OF THE INVENTION

The invention in its broadest aspects relates to the mercaptoacyl-4-substituted prolines of formula I above, to compositions containing such compounds and to the method of using such compounds as antihypertensive agents.

The term lower alkyl as used in defining the symbols R, $R_2$ and $R_3$ are straight or branched chain hydrocarbon radicals having up to seven carbons, for example, methyl, ethyl, propyl, isopropyl, butyl, isobutyl, t-butyl, pentyl, isopentyl, etc. The preferred lower alkyl groups are up to four carbons with methyl and ethyl most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclohexyl being most preferred.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term hydrolyzably removing protecting group employed in defining $R_4$ refers to a group that can be removed by conventional hydrolysis or ammonolysis. Acyl groups of the formula $$R_6-\overset{O}{\underset{\|}{C}}-$$

are suitable for this purpose wherein $R_6$ can be lower alkyl of 1 to 6 carbons, lower alkyl substituted with one or more chloro, bromo or fluoro groups, $-(CH_2)_m$-cycloalkyl, an aryl group such as

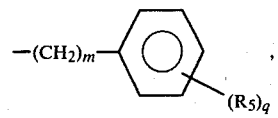

a hetero group such as

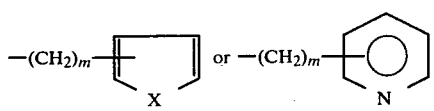

wherein m, $R_5$, q and X are as defined above. Preferred protecting groups are the lower alkanoyl groups having up to four carbons, especially acetyl, and benzoyl.

The term chemically removable protecting group employed in defining $R_4$ refers to groups such as p-methoxybenzyl, p-methoxybenzyloxycarbonyl, t-butoxycarbonyl, etc. These groups can be removed without effecting the remainder of the molecule such as by treatment with trifluoroacetic acid and anisole.

As shown in formula I, the substituent $R_1$ is in the cis-configuration with respect to the asymmetric center in the proline ring which is in the L-configuration. Of course, an additional asymmetric center can be present in the mercapto sidechain depending upon the substituents $R_2$ and $R_3$. The products of formula I can accordingly exist in stereoisomeric forms or as racemic mixtures thereof. All of these are within the scope of the invention. The synthesis described below can utilize the racemate or one of the enantiomers as starting materials. When the racemic starting material is used in the synthesis procedure, the stereoisomers obtained in the final product can be separated by conventional chromatographic or fractional crystallization methods. Preferably, if there is an asymmetric center in the mercaptoacyl sidechain, it is in the D-configuration.

Preferred compounds of formula I are those wherein R is hydrogen; $R_1$ is cyclohexyl or

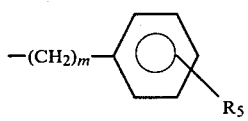

wherein m is zero, one or two, and $R_5$ is hydrogen, methyl, methoxy, methylthio, chloro, fluoro, trifluoromethyl or hydroxy; $R_2$ is hydrogen, methyl, trifluoromethyl, or methylthio; $R_3$ is hydrogen; n is zero or one; and $R_4$ is hydrogen. Also preferred as intermediates are the above compounds wherein $R_4$ is acetyl or benzoyl, especially acetyl.

The compounds of formula I are obtained by coupling the 4-cis substituted proline of the formula

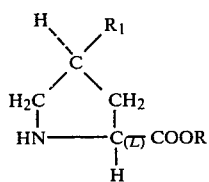

with an acid or its chemical equivalent of the formula

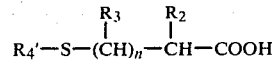

wherein $R'_4$ is hydrogen, $R_6$—CO—, or a chemically removable protecting group to yield the product of the formula

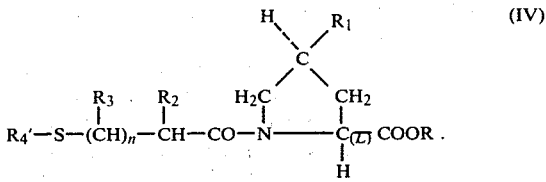

This reaction can be effected in the presence of a coupling agent such as dicyclohexylcarbodiimide or the like, or the acid can be activated by formation of its mixed anhydride, symmetrical anhydride, acid halide, active ester or use of Woodward reagent K, N-ethoxycarbonyl-2-ethoxyl-1,2-ethoxy-1,2-dihydroquinoline or the like. For a review of the methods of acylation, see Methoden der Organischchen Chemie (Houben-Weyl), Vol. XV, part II, page 1 et seq. (1974). Preferably, the acid halide, especially the acid chloride, of formula III is reacted with the acid of formula II.

If the proline of formula II is reacted in the ester from the resulting ester product of formula IV, i.e., R is alkyl, can be converted to the free acid, i.e., R is hydrogen, by conventional means. For example, if R is t-butyl this ester protecting group can be removed by treatment with trifluoroacetic acid and anisole.

The product of formula IV is preferably isolated and purified by crystallization, e.g., by forming the dicyclohexylamine salt and then converting the salt to the free acid form by treatment with an aqueous solution of an acid, such as potassium acid sulfate.

The product of formula IV bearing the acyl group $R_6$—CO— can be converted to the products of formula I wherein $R_4$ is hydrogen by conventional hydrolysis or by ammonolysis.

The products of formula I wherein $R_4$ is

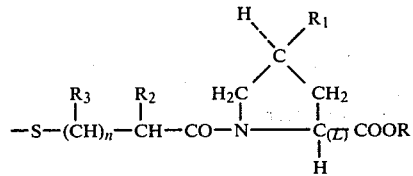

are obtained by directly oxidizing with iodine a product of formula I wherein $R_4$ is hydrogen.

The esters of formula I wherein R is lower alkyl can be obtained from the carboxylic acid compounds, i.e., wherein R is hydrogen, by conventional esterification procedures, e.g., by esterification with a diazomethane, a 1-alkyl-3-p-tolyltriazene, such as 1-n-butyl-3-p-tolyltriazene, etc. or by reaction with an alcohol in the presence of sulfuric acid.

The 4-cis substituted proline intermediates of formula II wherein $R_1$ is

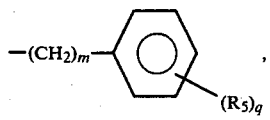

—(CH$_2$)$_m$-cycloalkyl,    —(CH$_2$)$_m$-(α-naphthyl),
—(CH$_2$)$_m$-(β-naphthyl),

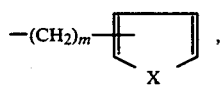

or

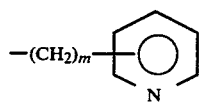

can be obtained by hydrogenating the corresponding 3,4-dehydro-4-substituted proline of the formula

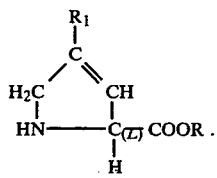

(V)

The preparation of these 3,4-dehydro-4-substituted prolines is disclosed in copending application U.S. Ser. No. 86,905. As disclosed therein, an N-protected 4-keto proline of the formula

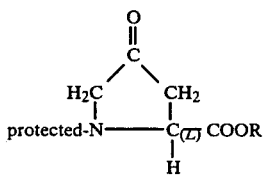

(VI)

wherein R is hydrogen or t-butyl is reacted with a solution of the Grignard or lithium reagent

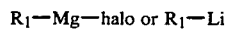

(VII)

wherein halo is Br or Cl and the N-protecting group is carbobenzyloxy or other suitable acyl protecting groups, to yield

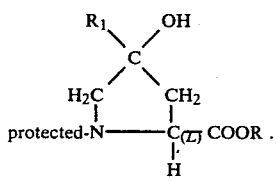

(VIII)

The compound of formula VIII will usually be obtained as a mixture of cis- and trans-hydroxy isomers with respect to the carboxylic acid or ester group. This mixture can be separated into the individual cis-hydroxy and trans-hydroxy isomers at this point of the synthetic procedure and the isomers can be purified by crystallization, by conversion to a salt form such as the 1-adamantanamine salt, or by chromatographic means.

The hydroxy intermediate of formula VIII is treated with a dehydrating agent such as p-toluene-sulfonic acid, sulfuric acid, potassium bisulfate, or trifluoroacetic acid to yield

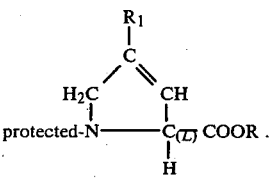

(IX)

The N-protecting group and the ester protecting groups if present can then be removed by conventional procedures to yield the dehydroproline of formula V. Alternatively, the dehydroproline of formula V can be obtained in a single step by treating the N-protected 4,4-disubstituted proline of formula VIII with a mixture of concentrated HCl and acetic acids and then neutralizing with ammonia.

The 4-cis substituted proline of formula II wherein R$_1$ is cyclohexyl are preferably prepared by hydrogenating the corresponding compound wherein R$_1$ is phenyl. Similarly, reduction of the 4-cis phenylproline intermediate of formula II with sodium or lithium in liquid ammonia according to the procedure of Weisenborn et al. in U.S. Pat. No. 3,485,819 yields the intermediate of formula II wherein R$_1$ is 1,4-cyclohexadienyl. Further hydrogenation of the resulting 4-cis-(1,4-cyclohexadienyl)-proline according to the procedure of Naito in U.S. Pat. No. 3,946,000 yields the corresponding 1-cyclohexenyl intermediate.

The intermediate of formula II wherein R$_1$ is

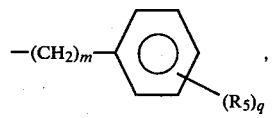

—(CH$_2$)$_m$-cycloalkyl,    —(CH$_2$)$_m$-(α-naphthyl),
—(CH$_2$)$_m$-(β-naphthyl),

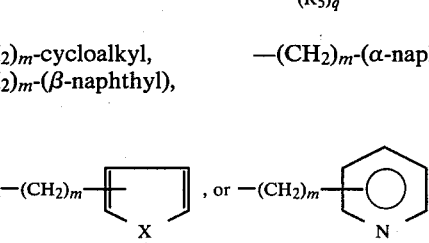

and m is other than zero can also be prepared by reacting the n-protected 4-keto proline of formula VI with a triphenylphosphorane of the formula

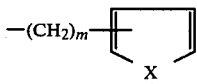

(X)

or a trialkylphosphorane of the formula

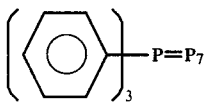

(alkyl)$_3$—P=P$_7$    (XI)

to yield the intermediate

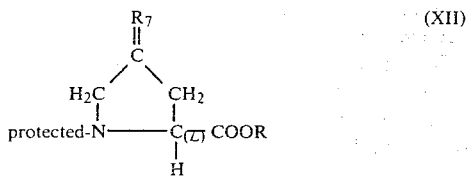

wherein $R_7$ is

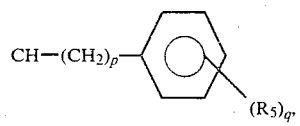

$CH\text{-}(CH_2)_p\text{-}(\alpha\text{-naphthyl})$, $CH\text{-}(CH_2)_p\text{-}(\beta\text{-naphthyl})$, $CH\text{-}(CH_2)_p\text{-cycloalkyl}$,

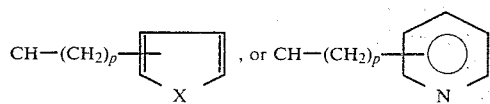

and p is zero, one or two. Hydrogenation of the intermediate of formula XII and removal of the N-protecting group and ester group if present by conventional procedures yields the 4-cis substituted proline of formula II.

The compounds of this invention form basic salts with a variety of inorganic or organic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose, for example, aralkylamines like, dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantanamine, benzathine, or salts derived from amino acids like arginine, lysine or the like. The physiologically acceptable salts like the sodium or potassium salts can be used medicinally as described below and are preferred. These and other salts which are not necessarily physiologically acceptable are useful in isolating or purifying a product acceptable for the purposes described below, as illustrated with the dicyclohexylamine salt in the examples. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compound of formula I wherein $R_4$ is hydrogen,

or the disulfide type substituent, especially wherein $R_4$ is hydrogen, are useful as hypotensive agents. They inhibit the conversion of the decapeptide angiotensin I to angiotensin II and, therefore, are useful in relieving angiotensin related hypertension. The action of the enzyme renin on angiotensin, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds, of formula I angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The preferred compounds of formula I as set forth above are particularly useful in treating hypertension because of their long duration of activity.

The compounds of this invention can also be formulated in combination with a diuretic for the treatment of hypertension. A combination product comprising a compound of this invention and a diuretic can be administered in an effective amount which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroglumethiazide, bendroflumethiazide, methchlothiazide, trichlormethiazide, polythiazide or benzthiazide, as well as ethacrynic acid, ticrynafen, chlorthalidone, furosemide, musolimine, bumetanide, triamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative process details are set forth in the following examples for the various reactions. These examples are preferred embodiments and also serve as models for the preparation of other compounds of this invention. The temperatures are given in degrees on the centigrade scale.

EXAMPLE 1

[1(S),4R]-1-[3-(Acetylthio)-2-methyl-1-oxopropyl]-4-phenyl-L-proline (a)

N-Carbobenzyloxy-cis-4-hydroxy-trans-4-phenyl-L-proline

65 Ml. of 3.2 M phenylmagnesium bromide in ether (0.21 mole) is added to a stirred solution of 23.8 g. (0.09 mole) of N-carbobenzyloxy-4-keto-L-proline (prepared according to Patchett et al., J. Amer. Chem. Soc., Vol. 79, p. 189–192) in 700 ml. of tetrahydrofuran over a period of 15 minutes while the temperature is maintained at 20°–25°. A gelatinous precipitate begins to separate after 45 ml. of the Grignard solution is added. After stirring overnight, most of the precipitate dissolves. The mixture is cooled to 15°, treated with a solution of 25 g. of ammonium chloride in 250 ml. of ice-water, stirred for one hour, and acidified with 35 ml. of 6 N hydrochloric acid. The organic phase is separated and the aqueous layer is extracted twice with 200 ml. of ethyl acetate. The organic phases are combined, dried ($MgSO_4$), filtered, and the solvent evaporated to give 32 g. of tan foam-like solid. This material is treated with 200 ml. of ether—125 ml. of N sodium hydroxide, shaken in a separatory funnel and filtered to remove the gelatinous material at the interface. The aqueous phase is separated, acidified with 22 ml. of 6 N hydrochloric acid and extracted with 100 ml. of ethyl acetate. The layers are separated and the aqueous phase is extracted twice with 50 ml. ethyl acetate. The organic phases are combined, dried ($MgSO_4$), filtered and the solvent evaporated to give 27.3 g. of a pale yellow foam-like residue. This material is treated with 150 ml. of ether to give a solution from which the product crystallizes. After cooling overnight, the mixture is filtered to give 11.8 g. of colorless solid, m.p. 120°–122°. Crystallization from 22 ml. of ethyl acetate—22 ml. of hexane yields 10.1 g. of N-carbobenzyloxy-cis-4-hydroxy-trans-4-phenyl-L-proline; m.p. 121°–123°; $[\alpha]_D^{25} -32°$ (c, 1% in $CHCl_3$). Additional product can be obtained by concentrating and cooling of the filtrate.

Anal. Calc'd. for $C_{19}H_{19}NO_5$: C, 66.85; H, 5.61; N, 4.10; Found: C, 66.67; H, 5.50; N, 3.99.

(b) N-Carbobenzyloxy-3,4-dehydro-4-phenyl-L-proline 8.0 g. (0.024 mole) of N-carbobenzyloxy-cis-4-hydroxy-trans-4-phenyl-L-proline is dissolved in 40 ml. of trifluoroacetic acid and the solution is kept overnight at room temperature. The bulk of the trifluoroacetic acid is removed on a rotary evaporator. The yellow-orange liquid residue (16 g.) is taken up in 80 ml. of methylene chloride, and washed with 40 ml. of water. After back-extracting the wash with 40 ml. of methylene chloride, the combined organic phases are dried ($MgSO_4$) and evaporated to give 8.5 g. of N-carbobenzyloxy-3,4-dehydro-4-phenyl-L-proline as a yellow-orange sticky residue.

(c) cis-4-Phenyl-L-proline, hydrochloride

A solution of 8.5 g. (0.024 mole) of N-carbobenzyloxy-3,4-dehydro-4-phenyl-L-proline in 180 ml. of methanol is treated with a slurry of 3.0 g. of 5% palladium-carbon catalyst in 20 ml. of water and shaken on a Parr hydrogenator for three hours under 3 atmospheres of hydrogen. The hydrogenation appears to be essentially completed within 45 minutes. The catalyst is filtered off under nitrogen, washed with methanol, and the combined filtrates, after treating with 25 ml. of N-hydrochloric acid, are evaporated, finally at 0.2 mm. The pinkish mostly solid residue is taken up in 200 ml. of methanol and the evaporation is repeated. After rubbing under 150 ml. of ether and again repeating the evaporation, the pink solid (5.5 g.) is triturated with 30 ml. of warm acetonitrile (most of the color entered the solvent) and cooled overnight to give 3.9 g. of pale pink solid of cis-4-phenyl-L-proline, hydrochloride; m.p. 115°–117° (foaming)(s. 109°); $[\alpha]_D^{25} +5°$ (c, 1% in methanol); $[\alpha]_D^{25} +26°$ (c, 1% in pyridine).

Anal. Calc'd. for $C_{11}H_{13}NO_2 \cdot HCl \cdot 0.75H_2O$: C, 54.77; H, 6.48; N, 5.81; Cl, 14.70; Found: C, 54.45; H, 6.47; N, 5.71; Cl, 14.88.

(d)

[1(S),4R]-1-[3-(Acetylthio)-2-methyl-1-oxopropyl]-4-phenyl-L-proline

A stirred suspension of 3.3 g. (0.0145 mole) of cis-4-phenyl-L-proline hydrochloride in 50 ml. of water is cooled to 5° and brought to pH 8.3 by the gradual addition of solid sodium carbonate (foam is broken up with the addition of a few drops of ether). Then while stirring and cooling, the murky solution is treated portionwise with 3.1 g. (0.0017 mole) of D-3-acetylthio-2-methylpropionyl chloride dissolved in 5 ml. of ether while maintaining the pH at from 7.4 to 8.3 by the dropwise addition of 20% sodium carbonate (wt./vol.). After the pH stabilizes at 8.3 (after about 15 minutes; the solution is now much clearer), stirring and cooling are continued for an hour (approximately 13 ml. of 20% sodium carbonate is consumed). The solution is then washed with 40 ml. of ethyl acetate (wash discarded), layered over with 40 ml. of fresh ethyl acetate, cooled, stirred, and acidified carefully with 6 N hydrochloric acid to pH 2, saturated with sodium chloride, and the layers are separated. The aqueous phase is extracted with additional ethyl acetate (3×40 ml.), the combined organic layers are dried ($MgSO_4$), and the solvent evaporated, finally at 0.2 mm., to give 4.3 g. of viscous yellow-orange product. This crude product is taken up in 30 ml. of warm ethyl acetate and treated with 2.4 g. of dicyclohexylamine in 5 ml. of ethyl acetate to give 4.9 g. (after cooling overnight) of the crystalline dicyclohexylamine salt; m.p. 177°–179° (s. 173°); $[\alpha]_D^{25} -46°$ (c, 1% in ethanol). Following crystallization of 4.8 g. of this material from 50 ml. of acetonitrile, 4.2 g. of colorless solid [1(S),4R]-1-[3-(acetylthio)-2-methyl-1-oxopropyl]-4-phenyl-L-proline, dicyclohexylamine salt are obtained; m.p. 179°–181° (s. 176°); $[\alpha]_D^{25} -47°$ (c, 1% in ethanol).

Anal. Calc'd. for: $C_{17}H_{21}NO_4S \cdot C_{12}H_{23}N$: C, 67.40; H, 8.58; N, 5.42; S, 6.21; Found: C, 67.45; H, 8.76; N, 5.38; S, 6.27.

The above dicyclohexylamine salt is converted to the free acid by suspending in 40 ml. of ethyl acetate, stirring, and treating with 50 ml. of 10% potassium bisulfate. After separating, the aqueous phase is extracted with ethyl acetate (3×40 ml.), the combined organic layers are dried ($MgSO_4$), and the solvent is evaporated. The residue is taken up in ether and the evaporation repeated, finally at 0.2 mm., to give 2.7 g. of [1(S),4R]-1-[3-(acetylthio)-2-methyl-1-oxopropyl]-4-phenyl-L-proline as a colorless, hygroscopic, foamy solid; $[\alpha]_D^{25} -74°$ (c, 1% in ethanol); $R_f$ 0.12 (85:15 toluene:acetic acid on silica gel; visualized with phosphomolybdic acid plus heat).

EXAMPLE 2

[1(S),4R]-1-(3-Mercapto-2-methyl-1-oxopropyl)-4-phenyl-L-proline

Argon is passed through a cold solution of 5.5 ml. of concentrated ammonium hydroxide in 13.5 ml. of water for 0.15 hours. This solution is then added while cooling and under a blanket of argon to 2.7 g. (0.008 mole) of [1-(S),4R]-1-[3-(acetylthio)-2-methyl-1-oxopropyl]-4-phenyl-L-proline. A solution is obtained almost immediately after stirring magnetically. After stirring at room temperature under argon for 1.5 hours, the solution is layered over with 30 ml. of ethyl acetate, cooled, stirred, and acidified carefully with 11 ml. of 6 N hydrochloric acid. (This and subsequent operations are carried out as much as possible under an argon atmosphere.) The layers are separated, the aqueous phase is extracted with ethyl acetate (3×30 ml.), the combined organic layers are dried (MgSO$_4$), and the solvent evaporated. The residue is taken up in ether and the evaporation repeated, finally at 0.2 mm, to give 2.3 g. of [1(S),4R]-1-(3-mercapto-2-methyl-1-oxopropyl)-4-phenyl-L-proline as a viscous gummy residue which sets to an amorphous brittle solid on standing; m.p. 52°–55° (s. 47°); $[\alpha]_D^{25}$ −55° (c, 1% in ethanol).

Anal. Calc'd. for $C_{15}H_{19}NO_3S.0.25H_2O$: C, 60.48; H, 6.60; N, 4.70; S, 10.76; Found: C, 60.37; H, 6.78; N, 4.79; S, 10.70.

EXAMPLE 3

[1(S),4R]-1-(3-Mercapto-2-methyl-1-oxopropyl)-4-[(4-methyl)phenyl]-L-proline

(a)

N-Carbobenzyloxy-4-hydroxy-4-[(4-methyl)phenyl]-L-proline

Following the procedure of Example 1(a) but substituting an equivalent amount of 4-methylphenyl magnesium bromide for the phenylmagnesium bromide one obtains N-carbobenzyloxy-4-hydroxy-4-[(4-methyl)phenyl]-L-proline.

(b) cis-4-[(4-Methyl)phenyl]-L-proline, hydrochloride

Treatment of N-carbobenzyloxy-4-hydroxy-4-[(4-methyl)phenyl]-L-proline with trifluoroacetic acid according to the procedure of Example 1(b) yields N-carbobenzyloxy-3,4-dehydro-4-[(4-methyl)phenyl]-L-proline.

This material is then hydrogenated and treated with hydrochloric acid according to the procedure of Example 1(c) to yield cis-4-[(4-methyl)phenyl]-L-proline, hydrochloride.

(c)

[1(S),4R]-1-[3-(Acetylthio)-2-methyl-1-oxopropyl]-4-[(4-methyl)phenyl]-L-proline A stirred suspension of cis-4-[(4-methyl)phenyl]-L-proline, hydrochloride is treated with D-3-acetylthio-2-methylpropionyl chloride according to the procedure of Example 1(d) to yield [1(S),4R]-1-[3-(acetylthio)-2-methyl-1-oxopropyl]-4-[(4-methyl)phenyl]-L-proline.

(d)

[1(S),4R]-1-(3-Mercapto-2-methyl-1-oxopropyl)-4-[(4-methyl)phenyl]-L-proline Treatment of [1(S),4R]-1-[3-acetylthio)-2-methyl-1-oxopropyl]-4-[(4-methyl)phenyl]-L-proline with concentrated ammonia according to the procedure of Example 2 yields [1(S),4R]-1-(3-mercapto-2-methyl-1-oxopropyl-4-[(4-methyl)phenyl]-L-proline.

EXAMPLE 4

(4S)-1-(3-Mercapto-1-oxopropyl)-4-(phenylpropyl)-L-proline

(a)

N-Carbobenzyloxy-4-hydroxy-4-(phenylpropyl)-L-proline

Following the procedure of Example 1(a) but substituting an equivalent amount of phenylpropyl magnesium bromide for the phenyl magnesium bromide one obtains N-carbobenzyloxy-4-hydroxy-4-(phenylpropyl)-L-proline.

(b) cis-4-(Phenylpropyl)-L-proline, hydrochloride

Treatment of N-carbobenzyloxy-4-hydroxy-4-(phenylpropyl)-L-proline with diazomethane in ether solution gives the methyl ester which is then dehydrated by treatment with a mixture of trifluoroacetic acid and trifluoroacetic anhydride. This product is then saponified to yield N-carbobenzyloxy-3,4-dehydro-4-(phenylpropyl)-L-proline.

This material is then hydrogenated and treated with hydrochloric acid according to the procedure of Example 1(c) to yield cis-4-(phenylpropyl)-L-proline, hydrochloride.

(c)

(4S)-1-[3-(Acetylthio)-1-oxopropyl]-4-(phenylpropyl)-L-proline

A stirred suspension of cis-4-(phenylpropyl)-L-proline, hydrochloride is treated with 3-acetylthiopropionyl chloride according to the procedure of Example 1(d) to yield (4S)-1-[3-(acetylthio)-1-oxopropyl]-4-(phenylpropyl)-L-proline.

(d)

(4S)-1-(3-Mercapto-1-oxopropyl)-4-(phenylpropyl)-L-proline

Treatment of (4S)-1-[3-(acetylthio)-1-oxopropyl]-4-(phenylpropyl)-L-proline with concentrated ammonia according to the procedure of Example 2 yields (4S)-1-(3-mercapto-1-oxopropyl)-4-(phenylpropyl)-L-proline.

EXAMPLE 5

[1(S),4R]-1-(3-Mercapto-2-methyl-1-oxopropyl)-4-[(2-methoxy)phenyl]-L-proline

(a)

N-Carbobenzyloxy-4-hydroxy-4-[(2-methoxy)phenyl]-L-proline

Following the procedure of Example 1(a) but substituting an equivalent amount of 2-methoxyphenyl magnesium bromide for the phenylmagnesium bromide one obtains N-carbobenzyloxy-4-hydroxy-4-[(2-methoxy)phenyl]-L-proline.

(b) cis-4-[(2-Methoxy)phenyl]-L-proline, hydrochloride

Treatment of N-carbobenzyloxy-4-hydroxy-4-[(2-methoxy)phenyl]-L-proline, hydrochloride with trifluoroacetic acid according to the procedure of Example 1(b) yields N-carbobenzyloxy-3,4-dehydro-4-[(2-methoxy)phenyl]-L-proline.

This material is then hydrogenated and treated with hydrochloric acid according to the procedure of Example 1(c) to yield cis-4-[(2-methoxy)phenyl]-L-proline, hydrochloride.

(c)
[1(S),4R]-1-[3-(Acetylthio)-2-methyl-1-oxopropyl]-4-[(2-methoxy)phenyl]-L-proline A stirred suspension of cis-4-[(2-methoxy)phenyl]-L-proline, hydrochloride is treated with D-3-acetylthio-2-methylpropionyl chloride according to the procedure of Example 1(d) to yield [1(S),4R]-[3-(acetylthio)-2-methyl-1-oxopropyl]-4-[(2-methoxy)phenyl]-L-proline.

(d)
[1(S),4R]-1-(3-Mercapto-2-methyl-1-oxopropyl)-4-[(2-methoxy)phenyl]-L-proline Treatment of [1(S),4R]-1-[3-(acetylthio)-2-methyl-1-oxopropyl]-4-[(2-methoxy)phenyl]-L-proline with concentrated ammonia according to the procedure of Example 2 yields [1(S),4R]-1-(3-mercapto-2-methyl-1-oxopropyl)-4-[(2-methoxy)phenyl]-L-proline.

EXAMPLE 6

[1(S),4R]-1-(3-Mercapto-2-methyl-1-oxopropyl)-4-[(2-hydroxy)phenyl]-L-proline

Treatment of [1(S),4R]-1-(3-mercapto-2-methyl-1-oxopropyl)-4-[(2-methoxy)phenyl]-L-proline with pyridine hydrochloride for one hour at 100° gives [1(S),4R]-1-(3-mercapto-2-methyl-1-oxopropyl)-4-[(2-hydroxy)phenyl]-L-proline.

EXAMPLE 7

[1(S),4R]-4-Cyclohexyl-1-(3-mercapto-2-methyl-1-oxopropyl)-L-proline, L-arginine salt (1:1)

(a) cis-4-Cyclohexyl-L-proline, hydrochloride

A solution of 4.1 g. (0.017 mole) of cis-4-phenyl-L-proline, hydrochloride in 150 ml. of ethanol is treated with 0.6 g. of platinum dioxide and shaken on a Parr hydrogenator for twenty four hours under 3 atmospheres of hydrogen. After filtering off the catalyst under nitrogen and washing with ethanol, the combined filtrates are dried on a rotary evaporator, finally at 0.2 mm. The foamy residue is rubbed under 100 ml of ether to give a solid and after repeating the evaporation the product is resuspended in 100 ml. of ether, cooled overnight, and filtered to yield 3.5 g. of colorless solid cis-4-cyclohexyl-L-proline, hydrochloride; m.p. 165°-167° (bubbles); (s. 145°); $[\alpha]_D^{25} - 16°$ (c, 1% in methanol).

Anal. Calc'd. for $C_{11}H_{19}NO_2.HCl.0.25H_2O$: C, 55.45; H, 8.67; N, 5.88; Cl, 14.88; Found: C, 55.70; H, 8.37; N, 5.81; Cl, 14.90.

(b)
[1(S),4R]-1-[3-(Acetylthio)-2-methyl-1-oxopropyl]-4-cyclohexyl-L-proline 3.4 g. (0.0145 mole) of cis-4-Cyclohexyl-L-proline, hydrochloride is reacted with 3.1 g. (0.017 mole) of D-3-acetylthio-2-methylpropionyl chloride in 70 ml. of water in the presence of sodium carbonate according to the procedure of Example 1(d) to yield 5.1 g. of a light yellow viscous product. This crude product is treated with 2.7 g. of dicyclohexylamine in 30 ml. of ethyl acetate to yield 6.2 g. of dicyclohexylamine salt; m.p. 189°-191° (s. 185°); $[\alpha]_D^{25} - 63°$ (c, 1% in ethanol). Following trituration with 60 ml. of boiling acetonitrile and cooling, 5.7 g. of colorless solid [1(S),4R]-1-[3-(acetylthio)-2-methyl-1-oxopropyl]-4-cyclohexyl-L-proline, dicyclohexylamine salt are obtained; m.p. 191°-193° (s. 188°); $[\alpha]_D^{25} - 64°$ (c, 1% in ethanol).

Anal. Calc'd. for $C_{17}H_{27}NO_4S.C_{12}H_{23}N$: C, 66.62; H, 9.64; N, 5.36; S, 6.13; Found: C, 66.42; H, 9.70; N, 5.30; S, 6.21.

The above dicyclohexylamine salt is converted to the free acid by suspending in 50 ml of ethyl acetate, stirring, and treating with 70 ml. of 10% potassium bisulfate. After separating, the aqueous phase is extracted with ethyl acetate (3×50 ml.), the combined organic layers are dried (MgSO4), and the solvent is evaporated. The residue is taken up in ether and the evaporation repeated, finally at 0.2 mm., to give 3.8 g. of [1(S),4R]-1-[3-(acetylthio)-2-methyl-1-oxopropyl]-4-cyclohexyl-L-proline as a colorless glass-like residue; $[\alpha]_D^{25} - 108°$ (c, 1% in ethanol); $R_f$ 0.49 (90:5:5 methylene chloride:methanol:acetic acid on silica gel; visualized iodine vapor, phosphomolybdic acid plus heat).

(c)
[1(S),4R]-4-Cyclohexyl-1-(3-mercapto-2-methyl-1-oxopropyl)-L-proline, arginine salt (1:1)

3.8 g. (0.011 mole) of the [1(S),4R]-1-[3-(acetylthio)-2-methyl-1-oxopropyl]-4-cyclohexyl-L-proline is hydrolyzed with 7.5 ml. of concentrated ammonium hydroxide in 18 ml. of water over a period of 1.25 hours as described in Example 2 to yield 3.2 g. of [1(S),4R]-4-cyclohexyl-1-(3-mercapto-2-methyl-1-oxopropyl)-L-proline as a colorless glass-like product; $[\alpha]_D^{25} - 85°$ (c, 1% in ethanol); $R_f$ 0.18 (85:15 toluene:acetic acid on silica gel; visualized phosphomolybdic acid plus heat, mercaptan reagent).

Anal. Calc'd for: $C_{15}H_{25}NO_3S.0.25H_2O$: C, 59.27; H, 8.40; N, 4.61; S, 10.55; Found: C, 59.19; H, 8.42; N, 4.87; S, 10.57.

A solution of 3.15 g. (0.010 mole) of the above product in 400 ml. of methanol is stirred under argon, treated with 1.85 g. (0.10 mole) of 98% L-arginine, and stirred until a solution is once again obtained. The methanol is removed on a rotary evaporator and the brittle residue is rubbed under 200 ml. of ether (evaporation repeated) to give a colorless solid. This material is resuspended in 200 ml. of ether, cooled for two hours, and filtered under argon to yield 4.6 g. of [1(S),4R]-4-cyclohexyl-1-(3-mercapto-2-methyl-1-oxopropyl)-L-proline, L-arginine salt (1:1); m.p. 126°-129° (foaming); (s, 98°); $[\alpha]_D^{25} - 45°$ (c, 1% in ethanol).

Anal. Calc'd. for: $C_{15}H_{25}NO_3S.C_6H_{14}N_4O_2.0.5H_2O$: C, 52.06; H, 8.35; N, 14.51; S, 6.64; Found: C, 51.77; H, 8.42; N, 14.89; S, 6.70.

EXAMPLE 8

[1(S),4R]-4-(1,4-Cyclohexadienyl)-1-(3-mercapto-2-methyl-1-oxopropyl)-L-proline (a) cis-4-(1,4-Cyclohexadienyl)-L-proline cis-4-Phenyl-L-proline is treated with lithium and ammonia according to the procedure of Example 1 of U.S. Pat. No. 3,485,819 to yield cis-4-(1,4-cyclohexadienyl)-L-proline.

(b)
[1(S),4R]-1-[3-(Acetylthio)-2-methyl-1-oxopropyl]-4-(1,4-cyclohexadienyl)-L-proline cis-4-(1,4-Cyclohexadienyl)-L-proline is reacted with D-3-acetylthio-2-methylpropionyl chloride according to the procedure of Example 1(d) to yield [1(S),4R]-1-

[3-(acetylthio)-2-methyl-1-oxopropyl]-4-(1,4-cyclohexadienyl)-L-proline.

(c) [1(S),4R]-4-(1,4-Cyclohexadienyl)-1-(3-mercapto-2-methyl-1-oxopropyl)-L-proline The product from part (b) is treated with concentrated ammonium hydroxide according to the procedure of Example 2 to yield [1(S),4R]-4-(1,4-cyclohexadienyl)-1-(3-mercapto-2-methyl-1-oxopropyl)-L-proline.

EXAMPLE 9

[1(S),4R]-4-(1-Cyclohexenyl)-1-(3-mercapto-2-methyl-1-oxopropyl)-L-proline (a) cis-4-(1-Cyclohexenyl)-L-proline cis-4-(1,4-Cyclohexadienyl)-L-proline is treated with a palladium-carbon catalyst and shaken on a Parr hydrogenator under 3 atmospheres of hydrogen to yield cis-4-(1-cyclohexenyl)-L-proline.

(b) [1(S),4R]-1-[3-(Acetylthio)-2-methyl-1-oxopropyl]-4-(1-cyclohexenyl)-L-proline cis-4-(1-Cyclohexenyl)-L-proline is reacted with D-3-acetylthio-2-methylpropionyl chloride according to tthe procedure of Example 1(d) to yield [1(S),4R]-1-[3-(acetylthio)-2-methyl-1-oxopropyl]-4-(1-cyclohexenyl)-L-proline.

(c) [1(S),4R]-4-(1-Cyclohexenyl)-1-(3-mercapto-2-methyl-1-oxopropyl)-L-proline

The product from part (b) is treated with concentrated ammonia according to the procedure of Example 2 to yield [1(S),4R]-4-(1-cyclohexenyl)-1-(3-mercapto-2-methyl-1-oxopropyl)-L-proline.

EXAMPLE 10

(4S)-1-(2-Mercapto-1-oxoethyl)-4-(2-thienyl)-L-proline (a) N-Carbobenzyloxy-4-hydroxy-4-(2-thienyl)-L-proline Following the procedure of Example 1(a) but substituting an equivalent amount of (2-thienyl) magnesium bromide for the phenylmagnesium bromide one obtains N-carbobenzyloxy-4-hydroxy-5-(2-thienyl)-L-proline.

(b) cis-4-(2-thienyl)-L-proline, hydrochloride

Treatment of N-carbobenzyloxy-4-hydroxy-4-(2-thienyl)-L-proline with trifluoroacetic acid according to the procedure of Example 1(c) yields N-carbobenzyloxy-3,4-dehydro-4-(2-thienyl)-L-proline.
This material is then hydrogenated and treated with hydrochloric acid according to the procedure of Example 1(c) to yield cis-4-(2-thienyl)-L-proline, hydrochloride.

(c) (4S)-1-[2-(Acetylthio)-1-oxxoethyl]-4-(2-thienyl)-L-proline

A stirred suspension of cis-4-(2-thienyl)-L-proline, hydrochloride is treated with 2-acetylthioacetyl chloride according to the procedure of Example 1(d) to yield (4S)-1-[2-(acetylthio)-1-oxoethyl]-4-(2-thienyl)-L-proline.

(d) (4S)-1-(2-Mercapto-1-oxoethyl)-4-(2-thienyl)-L-proline

Treatment of (4S)-1-[2-(acetylthio)-1-oxoethyl]-4-(2-thienyl)-L-proline with concentrated ammonia according to the procedure of Example 2 yields (4S)-1-(2-mercapto-1-oxoethyl)-4-(2-thienyl)-L-proline.

EXAMPLE 11

[1(S),4R]-1-(3-Mercapto-2-ethyl-1-oxopropyl)-4-(3-thienyl)-L-proline (a) N-carbobenzyloxy-4-hydroxy-4-(3-thienyl)-L-proline Following the procedure of Example 1(a) but substituting an equivalent amount of (3-thienyl) magnesium bromide for the phenylmagnesium bromide one obtains N-carbobenzyloxy-4-hydroxy-4-(3-thienyl)-L-proline.

(b) cis-4-(3-thienyl)-L-proline, hydrochloride

Treatment of N-carbobenzyloxy-4-hydroxy-4-(3-thienyl)-L-proline with trifluoroacetic acid according to the procedure of Example 1(c) yields N-carbobenzyloxy-3,4-dehydro-4-(3-thienyl)-L-proline.
This material is then hydrogenated and treated with hydrochloric acid according to the procedure of Example 1(c) to yield cis-4-(3-thienyl)-L-proline, hydrochloride.

(c) [1(S),4R]-1-[3-(Acetylthio)-2-ethyl-1-oxopropyl]-4-(3-thienyl)-L-proline

A stirred suspension of cis-4-(3-thienyl)-L-proline, hydrochloride is treated with D-3-acetylthio-2-ethylpropionyl chloride according to the procedure of Example 1(d) to yield [1(S),4R]-1-[3-(acetylthio)-2-ethyl-1-oxopropyl]-4-(3-thienyl)-L-proline.

(d) [1(S),4R]-1-(3-Mercapto-2-ethyl-1-oxopropyl)-4-(3-thienyl)-L-proline

Treatment of [1(S),4R]-1-[3-(acetylthio)-2-ethyl-1-oxopropyl]-4-(3-thienyl)-L-proline with concentrated ammonia according to the procedure of Example 2 yields [1(S),4R]-1-(3-mercapto-2-ethyl-1-oxopropyl)-4-(3-thienyl)-L-proline.

EXAMPLE 12

[1(S),4S]-1-(4-Mercapto-2-methyl-1-oxobutyl)-4-(2-furyl)-L-proline (a) N-Carbobenzyloxy-4-hydroxy-4-(2-furyl)-L-proline Following the procedure of Example 1(a) but substituting an equivalent amount of (2-furyl) magnesium bromide for the phenylmagnesium bromide one obtains N-carbobenzyloxy-4-hydroxy-4-(2-furyl)-L-proline.

(b) cis-4-(2-Furyl)-L-proline, hydrochloride

Treatment of N-carbobenzyloxy-4-hydroxy-4-(2-furyl)-L-proline with trifluoroacetic acid according to the procedure of Example 1(c) yields N-carbobenzyloxy-3,4-dehydro-4-(2-furyl)-L-proline.
This material is then hydrogenated and treated with hydrochloric acid according to the procedure of Example 1(c) to yield cis-4-(2-furyl)-L-proline, hydrochloride.

(c)
[1(S),4S]-1-[4-(Acetylthio)-2-methyl-1-oxobutyl]-4-(2-furyl)-L-proline

A stirred suspension of cis-4-(2-furyl)-L-proline, hydrochloride is treated with D-4-acetylthio-2-methylbutyroyl chloride according to the procedure of Example 1(d) to yield [1(S),4S]-1-[4-(acetylthio)-2-methyl-1-oxobutyl]-4-(2-furyl)-L-proline.

(d)
[1(S),4S]-1-[4-Mercapto-2-methyl-1-oxobutyl]-4-(2-furyl)-L-proline

Treatment of [1(S),4S]-1-[4-(acetylthio)-2-methyl-1-oxobutyl]-4-(2-furyl)-L-proline with concentrated ammonia according to the procedure of Example 2 yields [1(S),4S]-1(4-mercapto-2-methyl-1-oxobutyl)-4-(2-furyl)-L-proline.

EXAMPLE 13
[1(S),4R]-1-(3-Mercapto-2-methyl-1-oxopropyl)-4-(3-furyl)-L-proline (a) N-Carbobenzyloxy-4-hydroxy-4-(3-furyl)-L-proline Following the procedure of Example 1(a) but substituting an equivalent amount fo (3-furyl) magnesium bromide for the phenylmagnesium bromide one obtains N-carbobenzyloxy-4-hydroxy-4-(3-furyl)-L-proline.

(b) cis-4-(3-Furyl)-L-proline, hydrochloride

Treatment of N-carbobenzyloxy-4-hydroxy-4-(3-furyl)-L-proline with trifluoroacetic acid according to the procedure of Example 1(c) yields N-carbobenzyloxy-3,4-dehydro-4-(3-furyl)-L-proline.

This material is then hydrogenated and treated with hydrochloric acid according to the procedure of Example 1(c) to yield cis-4-(3-furyl)-L-proline, hydrochloride.

(c)
[1(S),4R]-1-[3-(Acetylthio)-2-methyl-1-oxopropyl]-4-(3-furyl)-L-proline

A stirred suspension of cis-4-(3-furyl)-L-proline, hydrochloride is treated with D-3-acetylthio-2-methylpropionyl chloride according to the procedure of Example 1(d) to yield [1(S),4R]-1-[3-(acetylthio)-2-methyl-1-oxopropyl]-4-(3-furyl)-L-proline.

(d)
[1(S),4R]-1-(3-Mercapto-2-methyl-1-oxopropyl)-4-(3-furyl)-L-proline

Treatment of [1(S),4R]-1-[3-(acetylthio)-2-methyl-1-oxopropyl]-4-(3-furyl)-L-proline with concentrated ammonia according to the procedure of Example 2 yields [1(S),4R]-1-(4-mercapto-2-methyl-1-oxopropyl)-4-(3-furyl)-L-proline.

EXAMPLE 14
[1(S),4R]-1-(3-Mercapto-2-methyl-1-oxopropyl)-4-(3-pyridyl)-L-proline (a)
N-Carbobenzyloxy-4-hydroxy-4-(3-pyridyl)-L-proline Following the procedure of Example 1(a) but substituting an equivalent amount of (3-pyridyl) magnesium bromide for the phenylmagnesium bromide one obtains N-carbobenzyloxy-4-hydroxy-4-(3-pyridyl)-L-proline.

(b) cis-4-(3-Pyridyl)-L-proline, hydrochloride

Treatment of N-carbobenzyloxy-4-hydroxy-4-(3-pyridyl)-L-proline with trifluoroacetic acid according to the procedure of Example 1(b) yields N-carbobenzyloxy-3,4-dehydro-4-(3-pyridyl)-L-proline.

This material is then hydrogenated and treated with hydrochloric acid according to the procedure of Example 1(c) to yield cis-4-(3-pyridyl)-L-proline, hydrochloride.

(c)
[1(S),4R]-1-[3-(Acetylthio)-2-methyl-1-oxopropyl]-4-(3-pyridyl)-L-proline

A stirred suspension of cis-4-(3-pyridyl)-L-proline, hydrochloride is treated with D-3-acetylthio-2-methylpropionyl chloride according to the procedure of Example 1(d) to yield [1(S),4R]-1-[3-(acetylthio)-2-methyl-1-oxopropyl]-4-(3-pyridyl)-L-proline.

(d)
[1(S),4R]-1-(3-Mercapto-2-methyl-1-oxopropyl)-4-(3-pyridyl)-L-proline

Treatment of [1(S),4R]-1-[3-(acetylthio)-2-methyl-1-oxopropyl]-4-(3-pyridyl)-L-proline with concentrated ammonia according to the procedure of Example 2 yields [1(S),4R]-1-(3-mercapto-2-methyl-1-oxopropyl)-4-(3-pyridyl)-L-proline.

EXAMPLE 15
[1(S),4R]-4-[(4-Phenyl)phenyl]-1-(3-mercapto-2-methyl-1-oxopropyl)-L-proline (a)
N-Carbobenzyloxy-4-[(4-phenyl)phenyl]-4-hydroxy-L-proline Following the procedure of Example 1(a) but substituting an equivalent amount of (4-phenyl)phenylmagnesium bromide for the phenylmagnesium bromide one obtains N-carbobenzyloxy-4-[4-(phenyl)phenyl]-4-hydroxy-L-proline.

(b) cis-4-[4-(phenyl)phenyl]-L-proline, hydrochloride

Treatment of N-carbobenzyloxy-4-[4-(phenyl)-phenyl]-4-hydroxy-L-proline with trifluoroacetic acid according to the procedure of Example 1(b) yields N-carbobenzyloxy-3,4-dehydro-4-[4-(phenyl)phenyl]-L-proline.

This material is then hydrogenated and treated with hydrochloric acid according to the procedure of Example 1(c) to yield cis-4-[4-(phenyl)phenyl]-L-proline, hydrochloride.

(c)
[1(S),4R]-1-[3-(Acetylthio)-2-methyl-1-oxopropyl]-4-[4-(phenyl)phenyl]-L-proline A stirred suspension of cis-4-[4-(phenyl)phenyl]-L-proline hydrochloride is treated with D-3-acetylthio-2-methylpropionyl chloride according to the procedure of Example 1(d) to yield [1(S),4R]-1-[3-(acetylthio)-2-methyl-1-oxopropyl]-4-[4-(phenyl)phenyl]-L-proline.

(d)
[1(S),4R]-4-[4-(Phenyl)phenyl]-1-(3-mercapto-2-methyl-1-oxopropyl)-L-proline Treatment of [1(S),4R]-1-[3-(acetylthio)-2-methyl-1-oxopropyl]-4-[4-(phenyl)phenyl]-L-proline with concentrated ammonia according to the procedure of Example 2 yields [1(S),4R]-4-[4-(phenyl)phenyl]-1-(3-mercapto-2-methyl-1-oxopropyl)-L-proline.

EXAMPLE 16

[1(S),4R]-4-[4-(Phenoxy)phenyl]-1-(3-mercapto-2-methyl-1-oxopropyl)-L-proline (a)
N-Carbobenzyloxy-4-[4-(phenoxy)phenyl]-4-hydroxy-L-proline Following the procedure of Example 1(a) but substituting an equivalent amount of (4-phenoxy)phenylmagnesium bromide for the phenylmagnesium bromide one obtains N-carbobenzyloxy-4-[4-(phenoxy)phenyl]-4-hydroxy-L-proline.

(b) cis-4-[4-(phenoxy)phenyl]-L-proline, hydrochloride

Treatment of N-carbobenzyloxy-4-[4-(phenoxy)phenyl]-4-hydroxy-L-proline with trifluoroacetic acid according to the procedure of Example 1(b) yields N-carbobenzyloxy-3,4-dehydro-4-[4-(phenoxy)phenyl]-L-proline.

This material is then hydrogenated and treated with hydrochloric acid according to the procedure of Example 1(c) to yield cis-4-[4-(phenoxy)phenyl]-L-proline, hydrochloride.

(c)
[1(S),4R]-1-[3-(Acetylthio)-2-methyl-1-oxopropyl]-4-[4-(phenoxy)phenyl]-L-proline A stirred suspension of cis-4-[4-(phenoxy)phenyl]-L-proline, hydrochloride is treated with D-3-acetylthio-2-methylpropionyl chloride according to the procedure of Example 1(d) to yield [1(S),4R]-1-[3-(acetylthio)-2-methyl-1-oxopropyl]-4-[4-(phenoxy)phenyl]-L-proline.

(d)
[1(S),4R]-1-(3-Mercapto-2-methyl-1-oxopropyl-4-[4-(phenoxy)phenyl]-L-proline Treatment of [1(S),4R]-1-[3-(acetylthio)-2-methyl-1-oxopropyl]-4-[4-(phenoxy)phenyl]-L-proline with concentrated ammonia according to the procedure of Example 2 yields [1(S),4R]-1-(3-mercapto-2-methyl-1-oxopropyl)-b 4-[4-(phenoxy)phenyl]-L-proline.

EXAMPLE 17

[1(S),4R]-1-(3-Mercapto-2-methyl-1-oxopropyl)-4-[4-(phenylthio)phenyl]-L-proline (a)
N-carbobenzyloxy-4-hydroxy-4-[4-(phenylthio)phenyl]-L-proline Following the procedure of Example 1 but substituting an equivalent of 4-(phenylthio)phenyllithium for the phenylmagnesium bromide one obtains N-carbobenzyloxy-4-hydroxy-4[4-(phenylthio)phenyl]-L-proline.

(b) cis-4-[(phenylthio)phenyl]-L-proline, hydrochloride

Treatment of N-carbobenzyloxy-4-hydroxy-4-[4-(phenylthio)phenyl]-L-proline with trifluoroacetic acid according to the procedure of Example 1(b) yields N-carbobenzyloxy-3,4-dehydro-4-[4-(phenylthio)phenyl]-L-proline.

This material is then hydrogenated and treated with hydrochloric acid according to the procedure of Example 1(c) to yield cis-4-[4-(phenylthio)phenyl]-L-proline, hydrochloride.

(c)
[1(S),4R]-1-[3-(Acetylthio)-2-methyl-1-oxopropyl]-4-[4-(phenylthio)phenyl]-L-proline A stirred suspension of cis-4-[4-(phenylthio)phenyl]-L-proline, hydrochloride is treated with D-3-acetylthio-2-methylpropionyl chloride according to the procedure of Example 1(d) to yield [1(S),4R]-1-[3-(acetylthio)-2-methyl-1-oxopropyl]-4-[4-(phenylthio)phenyl]-L-proline.

(d)
[1(S),4RR]-1-(3-Mercapto-2-methyl-1-oxopropyl)-4-[4-(phenylthio)phenyl]-L-proline Treatment of [1(S),4R]-1-[3-(acetylthio)-2-methyl-1-oxopropyl]-4-[4-(phenylthio)phenyl]-L-proline with concentrated ammonia according to the procedure of Example 2 yields [1(S),4R]-1-(3-mercapto-2-methyl-1-oxopropyl)-4-[4-(phenylthio)phenyl]-L-proline.

EXAMPLE 18

[1(S),4R]-1-(3-Mercapto-2-methyl-1-oxopropyl)-4-[4-(phenylmethyl)phenyl]-L-proline (a)
N-Carbobenzyloxy-4-[4-(phenylmethyl)phenyl]-4-hydroxy-L-proline Following the procedure of Example 1(a) but substituting an equivalent amount of 4-(phenylmethyl)phenyl] lithium for the phenylmagnesium bromide one obtains N-carbobenzyloxy-4-[4-(phenylmethyl)phenyl]-4-hydroxy-L-proline.

(b) cis-4-[4-(Phenylmethyl)phenyl]-L-proline, hydrochloride

Treatment of N-carbobenzyloxy-4-[4-(phenylmethyl)phenyl]-4-hydroxy-L-proline with trifluoroacetic acid according to the procedure of Example 1(b) yields N-carbobenzyloxy-3,4-dehydro-4-[4-(phenylmethyl)phenyl]-L-proline.

This material is then hydrogenated and treated with hydrochloric acid according to the procedure of Example 1(c), to yield cis-4-[4-(phenylmethyl)phenyl]-L-proline, hydrochloride.

[1(S),4R]-1-[3-(Acetylthio)-2-methyl-1-oxopropyl]-4-[4-(phenylmethyl)phenyl]-L-proline A stirred suspension of cis-4-[4-(phenylmethyl)phenyl]-L-proline, hydrochloride is treated with D-3-acetylthio-2-methylpropionyl chloride according to the procedure of Example 1(d) to yield [1(S),4R]-1-[3-(acetylthio)-2-methyl-1-oxopropyl]-4-[4-(phenylmethyl)phenyl-L-proline.

(d)
[1(S),4R]-1-(3-Mercapto-2-methyl-1-oxopropyl)-4-[4-(phenylmethyl)phenyl]-L-proline Treatment of [1(S),4R]-1-[3-(acetylthio)-2-methyl-1-oxopropyl]-4-[4-(phenylmethyl)phenyl]-L-proline with concentrated ammonia according to the procedure of Example 2 yields [1(S),4R]-1-(3-mercapto-2-methyl-1-oxopropyl)-4-[(4-phenylmethyl)phenyl]-L-proline.

EXAMPLE 19

[1(S),4R]-1-(3-Mercapto-2-methyl-1-oxopropyl)-4-(α-naphthyl)-L-proline (a) N-Carbobenzyloxy-4-hydroxy-4-(α-naphthyl)-L-proline Following the procedure of Example 1 but substituting an equivalent amount of α-naphthylmagnesium bromide for the phenylmagnesium bromide one obtains N-carbobenzyloxy-4-hydroxy-4-(α-naphthyl)-L-proline.

(b) cis-4-(α-Naphthyl)-L-proline, hydrochloride

Treatment of N-carbobenzyloxy-4-hydroxy-4-(α-naphthyl)-L-proline with trifluoroacetic acid according to the procedure of Example 1(b) yields N-carbobenzyloxy-3,4-dehydro-4-(α-naphthyl)-L-proline. This material is then hydrogenated and treated with hydrochloric acid according to the procedure of Example 1(c) to yield cis-4-(α-naphthyl)-L-proline, hydrochloride.

[1(S),4R]-1-[3-(Acetylthio)-2-methyl-1-oxopropyl]-4-(α-naphthyl)-L-proline

A stirred suspension of cis-4-(α-naphthyl)-L-proline, hydrochloride is treated with D-3-acetylthio-2-methylpropionyl chloride according to the procedure of Example 1(d) to yield [1(S),4R]-1-[3-(acetylthio)-2-methyl-1-oxopropyl]-4-(α-naphthyl)-L-proline.

(d) [1(S),4R]-1-(3-Mercapto-2-methyl-1-oxopropyl)-4-(α-naphthyl)-L-proline

Treatment of [1(S),4R]-1-[3-(acetylthio)-2-methyl-1-oxopropyl]-4-(α-naphthyl)-L-proline with concentrated ammonia according to the procedure of Example 2 yields [1(S),4R]-1-(3-mercapto-2-methyl-1-oxopropyl)-4-(α-naphthyl)-L-proline.

EXAMPLE 20

(4R)-1-(3-Mercapto-1-oxopropyl)-4-(β-naphthyl)-L-proline (a) N-Carbobenzyloxy-4-hydroxy-4-(β-naphthyl)-L-proline Following the procedure of Example 1 but substituting an equivalent amount of β-naphthylmagnesium bromide for the phenylmagnesium bromide one obtains N-carbobenzyloxy-4-hydroxy-4-(β-naphthyl)-L-proline.

(b) cis-4-(β-Naphthyl)-L-proline, hydrochloride

Treatment of N-carbobenzyloxy-4-hydroxy-4-(β-naphthyl)-L-proline with trifluoroacetic acid according to the procedure of Example 1(b) yields N-carbobenzyloxy-3,4-dehydro-4-(β-naphthyl)-L-proline. This material is then hydrogenated and treated with hydrochloric acid according to the procedure of Example 1(c), to yield cis-4-(β-naphthyl)-L-proline, hydrochloride.

(c) (4R)-1-[3-(Acetylthio)-1-oxopropyl]-4-(β-naphthyl)-L-proline

A stirred suspension of cis-4-(β-naphthyl)-L-proline, hydrochloride is treated with 3-acetylthiopropionyl chloride according to the procedure of Example 1(d) to yield (4R)-1-[3-(acetylthio)-1-oxopropyl]-4-(β-naphthyl)-L-proline.

(d) (4R)-1-(3-Mercapto-1-oxopropyl)-4-(β-naphthyl)-L-proline

Treatment of (4R)-1-[3-(acetylthio)-1-oxopropyl]-4-(β-naphthyl)-L-proline with concentrated ammonia according to the procedure of Example 2 yields (4R)-1-(3-mercapto-1-oxopropyl)-4-(β-naphthyl)-L-proline.

EXAMPLE 21

[1(S),4R]-1-(3-Mercapto-2-trifluoromethyl-1-oxopropyl)-4-phenyl-L-proline (a) 3-[[(4-Methoxy)phenylmethyl]thio]-2-trifluoromethylpropionyl chloride A neat mixture of 1-trifluoromethylacrylic acid (3.9 g.) and 4-methoxybenzylthiol (4.3 g.) is stirred at 100°–110° for one hour. The mixture is allowed to cool to room temperature and the solid is recrystallized from cyclohexane to yield 3-[[(4-methoxy)phenylmethyl]thio]-2-trifluoromethylpropanoic acid; m.p. 72°–74°.

Treatment of this acid with thionyl chloride yields 3-[[(4-methoxy)phenylmethyl]thio]-2-trifluoromethylpropionyl chloride.

(b) [1(S),4R]-1-[3-[[(4-Methoxy)phenylmethyl]thio]-2-trifluoromethyl-1-oxopropyl]-4-phenyl-L-proline The 3-[[(4-methoxy)phenylmethyl]thio]-2-trifluoromethylpropionyl chloride is reacted with cis-4-phenyl-L-proline, hydrochloride to yield [1(S),4R]-1-[3-[[(4-methoxy)phenylmethyl]thio]-2-trifluoromethyl-1-oxopropyl]-4-phenyl-L-proline.

(c) [1(S),4R]-1-(3-Mercapto-2-trifluoromethyl-1-oxopropyl)-4-phenyl-L-proline

The [1(S),4R]-1-[3-[[4-methoxy)phenylmethyl]thio]-2-trifluoromethyl-1-oxopropyl]-4-phenyl-L-proline is mixed with trifluoroacetic acid and anisole under nitrogen. The solvents are removed under vacuum to yield as a residue [1(S),4R]-1-(3-mercapto-2-trifluoromethyl-1-oxopropyl)-4-phenyl-L-proline.

EXAMPLE 22

[1(S),4R]-1-(3-Mercapto-2-methylthio-1-oxopropyl)-4-phenyl-L-proline (a) 3-[[(4-Methoxy)phenylmethyl]thio]-2-methylthiopropionyl chloride 3-[[(4-Methoxy)phenylmethyl]thio]-2-methylthiopropanoic acid prepared according to the procedure of Example 10 in U.S. Pat. No. 4,116,962 is treated with thionyl chloride to yield 3-[[(4-methoxy)phenylmethyl]thio]-2-methylthiopropionyl chloride.

(b) [1(S),4R]-1-[3-[[4-Methoxy)phenylmethyl]thio]-2-methylthio-1-oxopropyl]-4-phenyl-L-proline The 3-[[(4-methoxy)phenylmethyl]thio]-2-methylthiopropionyl chloride from part (a) is reacted with cis-4-phenyl-L-proline, hydrochloride to yield [1(S),4R]-1-

[[(4-methoxy)phenylmethyl]thio]-2-methylthio-1-oxopropyl]-4-phenyl-L-proline.

(c)
[1(S),4R]-1-(3-Mercapto-2-methylthio-1-oxopropyl)-4-phenyl-L-proline

The [1(S),4R]-1-[3-[[(4-methoxy)phenylmethyl]thio]-2-methylthio-1-oxopropyl]-4-phenyl-L-proline is mixed with trifluoroacetic acid and anisole under nitrogen. The solvents are removed under vacuum to yield as a residue [1(S),4R]-1-(3-mercapto-2-methylthio-1-oxopropyl)-4-phenyl-L-proline.

EXAMPLE 23

[1(S),4S]-B
1-(3-Mercapto-2-methyl-1-oxopropyl)-4-(phenylethyl)-L-proline (a)
N-Carbobenzyloxy-4-hydroxy-4-(phenylethyl)-L-proline Following the procedure of Example 1(a) but substituting an equivalent amount of (phenylethyl) magnesium bromide for the phenylmagnesium bromide one obtains N-carbobenzyloxy-4-hydroxy-4-phenylethyl-L-proline.

(b) cis-4-(Phenylethyl)-L-proline, hydrochloride

Treatment of N-carbobenzyloxy-4-hydroxy-4-(phenylethyl)-L-proline according to the procedure of Example 4(b) yields N-carbobenzyloxy-3,4-dehydro-4-(phenylethyl)-L-proline.
This material is then hydrogenated and treated with hydrochloric acid according to the procedure of Example 1(c) to yield cis-4-(phenylethyl)-L-proline, hydrochloride.

(c)
[1(S),4S]-1-[3-(Acetylthio)-2-methyl-1-oxopropyl]-4-(phenylethyl)-L-proline

A stirred suspension of cis-4-(phenylethyl)-L-proline, hydrochloride is treated with D-3-acetylthio-2-methylpropionyl chloride according to the procedure of Example 1(d) to yield [1(S),4S]-1-[3-(acetylthio)-2-methyl-1-oxopropyl]-4-(phenylethyl)-L-proline.

(d)
[1(S),4S]-1-(3-Mercapto-2-methyl-1-oxopropyl)-4-(phenylethyl)-L-proline

Treatment of [1(S),4S]-1-[3-(acetylthio)-2-methyl-1-oxopropyl]-4-(phenylethyl)-L-proline with concentrated ammonia according to the procedure of Example 2 yields [1(S),4S]-1-(3-mercapto-2-methyl-1-oxopropyl)-4-(phenylethyl)-L-proline.

EXAMPLE 24

[1(S),4S]-1-(3-Mercapto-2-methyl-1-oxopropyl)-4-(phenylmethyl)-L-proline (a) N-Carbobenzyloxy-4-(phenylmethylene)-L-proline To a 1 liter flask are added 7.6 g. (0.16 mole) of sodium hydride (50% suspension) and 150 ml. of dry dimethylsulfoxide. The suspension is stirred and then maintained at 70° for thirty minutes (all of the sodium hydride has reacted at this point). The solution is cooled to 30° and treated portionwise with a suspension of 61.1 g. (0.16 mole) of benzyltriphenylphosphonium chloride (dried in vacuo overnight) in 150 ml. dimethylsulfoxide and the resulting intense red suspension is heated to 70°. This mixture is cooled to 25° and treated with a solution of 13.2 g. (0.05 mole) of N-carbobenzyloxy-4-keto-L-proline in 40 ml. of dimethylsulfoxide over a period of twenty minutes. This mixture is maintained at 65°–70° for four hours, allowed to stand overnight at room temperature, and then poured onto a solution of 10 g. of potassium bicarbonate in 400 ml. of ice-water. Some ice is added to the mixture to bring the volume to 1 liter and it is then extracted three times with 250 ml. portions of ether. The ether phases are discarded and the aqueous phase is cooled and acidified with 50 ml. of 6 N hydrochloric acid. The product is extracted with 250 ml. of chloroform and then twice with 100 ml. of chloroform. The organic phases are combined, dried (MgSO$_4$), filtered and the solvent evaporated to give 102 g. of pale brown viscous residue. The latter is triturated with 500 ml. of ether. The ether is decanted from the brown residue (mostly triphenylphosphineoxide) and the latter is triturated twice with 100 ml. of ether. The ether phases are combined, cooled and treated portionwise with a solution of 10 g. of sodium bicarbonate in 200 ml. of water. The layers are separated and the organic phase is extracted with 10 ml. of water. The ether phase is discarded and the aqueous phases are combined, cooled, acidified with 18 ml. of 6 N hydrochloric acid and extracted three times with 100 ml. of ether. The organic layers are combined, dried (MgSO$_4$), filtered and the solvent evaporated to give 8.9 g. (52.6%) of a pale yellow foam. The bulk of this compound (8.6 g.) is dissolved in 20 ml. of acetonitrile and treated with 4.6 g. of dicyclohexylamine. The product slowly crystallizes. After standing overnight in the cold, the nearly colorless dicyclohexylamine salt is filtered and dried to yield 11.0 g. of N-carbobenzyloxy-4-(phenylmethylene)-L-proline, dicyclohexylamine; m.p. 142°–150°. After recrystallization from 65 ml. of acetonitrile, 9.5 g. of nearly colorless dicyclohexylamine salt are obtained; m.p. 150°–155°; $[\alpha]_D^{25}$ +7.7° (c, 1% in chloroform).

Anal. Calc'd. for C$_{20}$H$_{19}$NO$_4$·C$_{12}$H$_{23}$N: C, 74.09; H 8.16; N, 5.40; Found: C, 73.87; H, 8.18; N, 5.33.

This dicyclohexylamine salt (9.4 g.) is suspended in 100 ml. of ethyl acetate and treated with 100 ml. of 10% potassium bisulfate. The mixture is shaken and the aqueous phase is extracted twice with 50 ml. of ethyl acetate. The organic phases are combined, dried (MgSO$_4$), filtered and the solvent evaporated to give 6.4 g. (38%) of pale yellow foam-like solid N-carbobenzyloxy-4-(phenylmethylene)-L-proline; $[\alpha]_D^{25}$ −2.5° (c, 1% in chloroform); R$_f$ 0.29 (85:15 toluene:acetic acid on silica gel).

(b) cis-4-(Phenylmethyl)-L-proline

A solution of 6.1 g. of N-carbobenzyloxy-4-(phenylmethylene)-L-proline in 200 ml. of ethyl acetate is treated with 0.6 g. of platinum dioxide. The mixture is shaken under one atmosphere of hydrogen. Initially the uptake of hydrogen is rapid and essentially ceases in thirty minutes. The colorless solution is filtered and the filtrate is concentrated to give 5.7 g. of N-carbobenzyloxy-cis-4-(phenylmethyl)-L-proline. The latter is dissolved in 200 ml. of methanol and 30 ml. of water and treated with a slurry of 2 g. of 5% palladium-carbon catalyst in 70 ml. of methanol. The mixture is shaken under two atmospheres of hydrogen. The uptake of hydrogen is essentially complete in forty minutes. After seventy minutes, the catalyst is filtered through a celite bed and the filtrate concentrated to give 3.3 g. (89%) of pale gray solid cis-4-(phenylmethyl)-L-proline; m.p. 200°–201° (dec.); $[\alpha]_D^{25}$ −3.5° (c, 1% in N-hydrochloric acid). A small amount off catalyst is present in this material.

Anal. Calc'd. for $C_{12}H_{15}NO_2 \cdot \frac{1}{4}H_2O$: C, 68.71; H, 7.45; N, 6.68; Found: C, 68.21; H, 7.62; N, 6.56.

(c)
[1(S),4S]-1-[3-(Acetylthio)-2-methyl-1-oxopropyl]-4-(phenylmethyl)-L-proline A stirred suspension of 2.4 g. (0.012 mole) of cis-4-(phenylmethyl)-L-proline in a solution of 1 g. of sodium carbonate in 40 ml. of water is cooled to 10° and treated with a solution of 2.2 g. (0.012 mole) of D-3-acetylthio-2-methylpropionyl chloride in 5 ml. of ether over a period of ten minutes. An additional 1.7 g. of sodium carbonate is added portionwise to the mixture during this period to maintain the pH at about 8. A solution is obtained. The ice-bath is removed and the solution is stirred for two hours at room temperature, cooled, 50 ml. of ethyl acetate are added and resulting mixture is acidified with 8 ml. of 6 N hydrochloric acid. The phases are separated and the aqueous phase is extracted twice with 25 ml. of ethyl acetate. The organic phases are combined, dried (MgSO₄), filtered, and the solvent evaporated to give 4.5 g. of a pale yellow viscous residue. The latter is dissolved in 20 ml. of ethyl acetate and treated with a solution of 2.3 g. of dicyclohexylamine in 5 ml. of ethyl acetate. The resulting solution is seeded and the dicyclohexylamine salt rapidly crystallizes. After cooling overnight, the nearly colorless solid weighs 3.8 g.; m.p. 167°–169° (s. 163°). This material is digested in 15 ml. of warm acetonitrile, cooled and filtered to give 3.5 g. of colorless solid; m.p. 167°–169°. After recrystallization from 45 ml. of acetonitrile 3.2 g. of [1(S),4R]-1-[3-(acetylthio)-2-methyl-1-oxopropyl]-4-(phenylmethyl)-L-proline, dicyclohexylamine salt are obtained; m.p. 169°–171°; $[\alpha]_D^{25}$ −80° (c, 1% in chloroform).

Anal. Calc'd. for $C_{18}H_{23}NO_4S \cdot C_{12}H_{23}N$: C, 67.88; H, 8.74; N, 5.28; S, 6.04; Found: C, 67.60; H, 8.95; N, 5.24; S, 6.00.

The purified dicyclohexylamine salt is converted to the free acid by suspending in 30 ml. of ethyl acetate and treating portionwise with 30 ml. of 10% potassium bisulfate solution. The layers are separated and the aqueous phase is extracted twice with 20 ml. of ethyl acetate. The organic phases are combined, dried (MgSO₄), filtered and the solvent evaporated to give 2.0 g. (49%) of foamy semi-solid [1(S),4S]-1-[3-(acetylthio)-2-methyl-1-oxopropyl]-4-(phenylmethyl)-L-proline; 8 $\alpha]_D^{25}$ −121°; $R_f$ 0.15 (85:15 toluene-acetic acid on silica gel).

(d)
[1(S),4S]-1-(3-Mercapto-2-methyl-1-oxopropyl)-4-(phenylmethyl)-L-proline 1.9 g. of [1(S),4S]-1-[3-(acetylthio)-2-methyl-1-oxopropyl]-4-(phenylmethyl)-L-proline, under argon, is treated with a cold solution of 5 ml. of concentrated ammonia in 12 ml. of water. The stirred mixture becomes a solution in several minutes, it is then allowed to stand at room temperature for ninety minutes, cooled, and extracted twice with 15 ml. of ethyl acetate. The aqueous phase is stirred, layered with 15 ml. of ethyl acetate, acidified with 10 ml. of 5 N hydrochloric acid and the layers are separated. The aqueous phase is extracted twice with 15 ml. of ethyl acetate. The organic phases are combined, dried (MgSO₄), filtered and the solvent evaporated to give a colorless foam. The latter is dissolved in 10 ml. of ether and the solvent is removed on a rotary evaporator to give 1.63 g. (96%) of [1(S),4S]-1-(3-mercapto-2-methyl-1-oxopropyl)-4-(phenylmethyl)-L-proline as a colorless foam; m.p. 43°–48° (s. 37°); $[\alpha]_D^{25}$ −85° (c, 1% in ethanol); $R_f$ 0.58 (90:5:5 methylene chloride:methanol:acetic acid on silica gel).

Anal. Calc'd. for $C_{16}H_{21}NO_3S \cdot \frac{1}{4}H_2O$: C, 61.61; H, 6.95; N, 4.49; S, 10.28; SH, 10.59; Found: C, 61.48; H, 7.10; N, 4.69; S, 10.35; SH, 10.57.

A sample of the above acid is dissolved in ethyl acetate and treated with 1-adamantanamine in ethyl acetate to precipitate [1(S),4S]-1-(3-mercapto-2-methyl 1-oxopropyl)-4-(phenylmethyl)-L-proline, 1-adamantanamine salt; m.p. 220°–222° (dec.).

EXAMPLE 25

[1(S),4S]-4-[(4-Fluorophenyl)methyl]-1-(3-Mercapto-2-methyl-1-oxopropyl)-L-proline, L-arginine salt (a) [(4-Fluorophenyl)methyl]triphenylphosphonium chloride A stirred solution of 79.0 g. (0.3 mole) of triphenylphosphine in 400 ml. of xylene is treated with 43.3 g. (0.3 mole) of 4-fluorobenzyl chloride. The resulting solution is heated (product begins to crystallize at this point) and refluxed for six hours. After standing overnight at room temperature, the solid is filtered, washed with xylene and then with ethyl acetate, and dried in a desiccator to yield 73.3 g. (60%) of [(4-fluorophenyl)methyl]-triphenylphosphonium chloride; m.p. 295°–298°.

(b)
N-Carbobenzyloxy-4-[(4-fluorophenyl)methylene]-L-proline

Interaction of 7.6 g. (0.16 mole) of sodium hydride (50% suspension) with 150 ml. dimethylsulfoxide, followed by treatment with 65.0 g. (0.16 mole) of [(4-fluorophenyl)methyl]triphenylphosphonium chloride and the reaction with 13.2 g. (0.05 mole) of N-carbobenzyloxy-4-keto-L-proline according to the procedure of Example 24(a) gives 7.0 g. (39%) of pale yellow N-carbobenzyloxy-4-[(4-fluorophenyl)methylene]-L-proline, $R_f$ 0.31 (85:15 toluene:acetic acid). This material is dissolved in 20 ml. of acetonitrile and treated with 3.6 g. of dicyclohexylamine. The dicyclohexylamine salt rapidly crystallizes from solution. After standing overnight in the cold, the product is filtered and washed with cold acetonitrile and ether to give 8.0 g. (30%) of colorless N-carbobenzyloxy-4-[(4-fluorophenyl)methylene]-L-proline, dicyclohexylamine salt, m.p. 159°–161°; $[\alpha]_D^{25}$ +7.0° (c, 1% in chloroform).

Anal. Calc'd. for $C_{20}H_{18}FNO_4 \cdot C_{12}H_{23}N \cdot \frac{1}{4}H_2O$: C, 71.02; H, 7.73; N, 5.18; F, 3.51, Found: C, 71.35; H, 7.86; N, 4.89; F, 3.14.

The above dicyclohexylamine salt (8.0 g.) is suspended in ethyl acetate and treated with 10% potassium bisulfate according to the procedure of Example 24(a) to give 5.3 g. of N-carbobenzyloxy-4-[(4-fluorophenyl)methylene]-L-proline as a pale yellow syrup.

(c) cis-4-[(4-Fluorophenyl)methyl]-L-proline

Hydrogenation of 5.1 g. of N-carbobenzyloxy-4-[(4-fluorophenyl)methylene]-L-proline according to the procedure of Example 24(b) give 3.0 g. (92%) of nearly colorless cis-4-[(4-fluorophenyl)methyl]-L-proline; m.p.

207°–209° (dec.); $[\alpha]_D^{25}$ −5.0° (c, 1% in N hydrochloric acid).

Anal. Calc'd. for $C_{12}H_{14}FNO_2 \cdot \frac{1}{4}H_2O$: C, 63.28; H, 6.42; N, 6.15; F, 8.34; Found: C, 63.28; H, 6.49; N, 6.13; F, 8.05.

(d)
[1(S),4S]-1-[3-(Acetylthio)-2-methyl-1-oxopropyl]-4-[(4-fluorophenyl)methyl]-L-proline Interaction of 2.7 g. (0.012 mole) of cis-4-[(4-fluorophenyl)methyl]-L-proline with 2.3 g. (0.013 mole) of D-3-acetylthio-2-methylpropionyl chloride in aqueous sodium carbonate solution according to the procedure of Example 24(c) gives 4.8 g. of pale yellow syrup. The latter is dissolved in 30 ml. of ethyl acetate and treated with 2.5 g. of dicyclohexylamine. The product rapidly crystallizes from solution. After cooling overnight, the colorless product is filtered and dried to yield 4.9 g. of crude salt product (74%); m.p. 177°–179° (s. 172°). This material is crystallized from 45 ml. of acetonitrile to give 4.3 g. of product; m.p. 176°–178°; $[\alpha]_D^{25}$ −67° (c, 1% in chloroform). After recrystallization from 35 ml. of acetonitrile, there are obtained 4.1 g. (62%) of colorless [1(S), 4S]-1-[3-(acetylthio)-2-methyl-1-oxopropyl]-4-[(4-fluorophenyl)methyl]-L-proline, dicyclohexylamine salt; m.p. 177°–179°; $[\alpha]_D^{25}$ −69° (c, 1% in chloroform).

Anal. Calc'd. for $C_{18}H_{22}FNO_4S \cdot C_{12}H_{23}N$: C, 65.66; H, 8.27; N, 5.11; F, 3.46; S, 5.84; Found: C, 65.78; H, 8.35; N, 5.13; F, 3.24; S, 5.79.

The purified dicyclohexylamine salt is converted to the free acid by suspending in ethyl acetate and treating with 10% potassium bisulfate according to the procedure of Example 24(c) to yield 2.7 g. (62%) of colorless hygroscopic [1(S),4S]-1-[3-(acetylthio)-2-methyl-1-oxopropyl]-4-[(4-fluorophenyl)methyl]-L-proline; m.p. 40°–45° (s. 35°); $[\alpha]_D^{25}$ −146.7° (c, 1% in chloroform).

(e)
[1(S),4S]-4-[(4-Fluorophenyl)methyl]-1-(3-mercapto-2-methyl-1-oxopropyl)-L-proline, L-arginine salt Treatment of 2.7 g. of [1(S),4S]-1-[3-(acetylthio)-2-methyl-1-oxopropyl]-4-[(4-fluorophenyl)methyl]-L-proline with aqueous ammonia according to the procedure of Example 24(d) gives 2.37 g. (100%) of [1(S),4S]-4-[(4-fluorophenyl)methyl]-1-(3-mercapto-2-methyl-1-oxopropyl)-L-proline as an extremely hydroscopic colorless foam; $[\alpha]_D^{25}$ −84.5° (c, 1% in ethanol); $R_f$ 0.54 (90:5:5 methylene chloride: methanol:acetic acid on silica gel).

Part of this material (2.17 g.) is dissolved in 100 ml. of methanol and added to a stirred suspension of 1.0 g. of L-arginine in 100 ml. of methanol. After stirring at room temperature for thirty minutes (all of the L-arginine is dissolved), the colorless solution is concentrated on a rotary evaporator to give a granular colorless solid. The latter is suspended in 200 ml. of ether and the material triturated with the solvent. The ether is removed and the residue (3.17 g.) is suspended in 100 ml. of ether, allowed to stand at room temperature overnight and filtered to give 2.9 g. (87%) of colorless solid [1(S),4S]-4-[(4-fluorophenyl)methyl]-1-(3-mercapto-2-methyl-1-oxopropyl)-L-proline, L-arginine salt; m.p. 124°–127°; $[\alpha]_D^{25}$ −47° (c, 1% in ethanol).

Anal. Calc'd. for $C_{16}H_{20}FNO_3S \cdot C_6H_{14}N_4O_2 \cdot \frac{1}{4}H_2O$: C, 52.42; H, 6.80; N, 13.89; F, 3.77; S, 6.36; —SH, 6.56; Found: C, 52.41; H, 7.05; N, 12.90; F, 3.33; S, 6.35; —SH, 6.37.

The [1(S),4S]-4-[(4-fluorophenyl)methyl]-1-(3-mercapto-2-methyl-1-oxopropyl)-L-proline is dissolved in ethyl acetate and treated with 1-adamantanamine to yield [1(S),4S]-4-[(4-fluorophenyl)methyl]-1-(3-mercapto-2-methyl-1-oxopropyl)-L-proline, 1-adamantanamine salt; m.p. 217°–219°.

Anal. Calc'd. for $C_{16}H_{20}FNO_3S \cdot C_{10}H_{17}N$: C, 65.52; H, 7.83; N, 5.88; Found: C, 66.55; H, 8.04; N, 5.73.

EXAMPLE 26

[1(S),4S]-1-(3-Mercapto-2-methyl-1-oxopropyl)-4-[(2-methoxyphenyl)methyl]-L-proline (a) [(2-Methoxyphenyl)methyl]triphenylphosphonium chloride Treatment of triphenylphosphine with 2-methoxybenzyl chloride according to the procedure of Example 25(a) yields [(2-methoxyphenyl)methyl]triphenylphosphonium chloride.

(b) cis-4-[(2-Methoxyphenyl)methyl]-L-proline

[(2-Methoxyphenyl)methyl]triphenylphosphonium chloride is reacted with sodium hydride in dimethylsulfoxide and then N-carbobenzyloxy-4-keto-L-proline according to the procedure of Example 24(a) to yield N-carbobenzyloxy-4-[(2-methoxyphenyl)methylene]-L-proline. Hydrogenation of this material according to the procedure of Example 24(b) yields cis-4-[(2-methoxyphenyl)methyl]-L-proline.

(c)
[1(S),4S]-1-[3-(Acetylthio)-2-methyl-1-oxopropyl]-4-[(2-methoxyphenyl)methyl]-L-proline Reaction of cis-4-[(2-methoxyphenyl)methyl]-L-proline with D-3-acetylthio-2-methylpropionyl chloride according to the procedure of Example 24(c) yields [1(S),4S]-1-[3-(acetylthio)-2-methyl-1-oxopropyl]-4-[(2-methoxyphenyl)methyl]-L-proline.

(d)
[1(S),4S]-1-(3-Mercapto-2-methyl-2-oxopropyl)-4-[(2-methoxyphenyl)methyl]-L-proline Treatment of [1(S),4S]-1-[3-(acetylthio)-2-methyl-1-oxopropyl]-4-[(2-methoxyphenyl)methyl]-L-proline with aqueous ammonia according to the procedure of Example 24(d) yields [1(S),4S]-1-(3-mercapto-2-methyl-1-oxopropyl)-4-[(2-methoxyphenyl)methyl]-L-proline.

EXAMPLE 27

[1(S),4S]-4-[(2-Hydroxyphenyl)methyl]-1-(3-mercapto-2-methyl-1-oxopropyl)-L-proline Treatment of [1(S),4S]-1-(3-mercapto-2-methyl-1-oxopropyl)-4-[(2-methoxyphenyl)methyl]-L-proline with pyridine hydrochloride for one hour at 100° gives [1(S),4S]-4-[(2-hydroxyphenyl)methyl]-1-(3-mercapto-2-methyl-1-oxopropyl)-L-proline.

EXAMPLE 28

[1(S),4S]-1-(3-Mercapto-2-methyl-1-oxopropyl)-4-[(4-Methylphenyl)methyl]-L-proline (a) [(4-Methylphenyl)methyl]triphenylphosphonium chloride Treatment of triphenylphosphine with 4-methylbenzyl chloride according to the procedure of Example 25(a) yields [(4-methylphenyl)methyl]triphenylphosphonium chloride.

(b) cis-4-[(4-Methylphenyl)methyl]-L-proline

[(4-Methylphenyl)methyl]triphenylphosphonium chloride is reacted with sodium hydride in dimethylsulfoxide and then N-carbobenzyloxy-4-keto-L-proline according to the procedure of Example 24(a) to yield N-carbobenzyloxy-4-[(4-methylphenyl)methylene]-L-proline. Hydrogenation of this material according to the procedure of Example 24(b) yields cis-4-[(4-methylphenyl)methyl]-L-proline.

(c) [1(S),4S]-1-[3-(Acetylthio)-2-methyl-1-oxopropyl]-4-[(4-methylphenyl)methyl]-L-proline Reaction of cis-4-[(4-methylphenyl)methyl]-L-proline with D-3-acetylthio-2-methylpropionyl chloride according to the procedure of Example 24(c) yields [1(S),4S]-1-[3-(acetylthio)-2-methyl-1-oxopropyl]-4-[(4-methylphenyl)methyl]-L-proline.

(d) [1(S),4S]-1-(3-Mercapto-2-methyl-1-oxopropyl)-4-[(4-methylphenyl)methyl]-L-proline Treatment of [1(S),4S]-1-[3-(acetylthio)-2-methyl-1-oxopropyl]-4-[(4-methylphenyl)methyl]-L-proline with aqueous ammonia according to the procedure of Example 24(d) yields [1(S),4S]-1-(3-mercapto-2-methyl-1-oxopropyl)-4-[(4-methylphenyl)methyl]-L-proline.

EXAMPLE 29

[1(S),4S]-1-(3-Mercapto-2-methyl-1-oxopropyl)-4-[(4-methylthiophenyl)propyl]-L-proline (a) [(4-Methylthiophenyl)propyl]triphenylphosphonium chloride Treatment of triphenylphosphine with (4-methylthiophenyl)propyl chloride according to the procedure of Example 25(a) yields [(4-methylthiophenyl)propyl]triphenylphosphonium chloride.

(b) cis-4-[(4-Methylthiophenyl)propyl]-L-proline

[(4-Methylthiophenyl)propyl]triphenylphosphonium chloride is reacted with sodium hydride in dimethylsulfoxide and then N-carbobenzyloxy-4-keto-L-proline, phenylmethyl ester according to the procedure of Example 24 (a) to yield N-carbobenzyloxy-4-[(4-methylthiophenyl)propylene]-L-proline phenylmethyl ester. Hydrogenation of this material according to the procedure of Example 24(b) yields cis-4-[(4-methylthiophenyl)propyl]-L-proline.

(c) [1(S),4S]-1-[3-(Acetylthio)-2-methyl-1-oxopropyl]-4-[(4-methylthiophenyl)propyl]-L-proline Reaction of cis-4-[(4-methylthiophenyl)propyl]-L-proline with D-3-acetylthio-2-methylpropionyl chloride according to the procedure of Example 24 (c) yields [1(S),4S]-1-[3-(acetylthio)-2-methyl-1-oxopropyl]-4-[(4-methylthiophenyl)propyl]-L-proline.

(d) [1(S),4S]-1-(3-Mercapto-2-methyl-1-oxopropyl)-4-[(4-methylthiophenyl)propyl]-L-proline Treatment of [1(S),4S]-1-[3-(acetylthio)-2-methyl-1-oxopropyl]-4-[(4-methylthiophenyl)propyl]-L-proline with aqueous ammonia according to the procedure of Example 24 (d) yields [1(S),4S]-1-(3-mercapto-2-methyl-1-oxopropyl)-4-[(4-methylthiophenyl)propyl]-L-proline.

EXAMPLE 30

(4S)-1-(4-Mercapto-1-oxobutyl)-4-[(3-trifluoromethylphenyl)methyl]-L-proline (a) [(3-Trifluoromethylphenyl)methyl]triphenylphosphonium chloride Treatment of triphenylphosphine with 3-trifluoromethylbenzyl chloride according to the procedure of Example 25 (a) yields [(trifluoromethylphenyl)methyl]triphenylphosphonium chloride.

(b) cis-4-[(3-Trifluoromethylphenyl)methyl]-L-proline

[(3-Trifluoromethylphenyl)methyl]triphenylphosphonium chloride is reacted with sodium hydride in dimethylsulfoxide and then N-carbobenzyloxy-4-keto-L-proline according to the procedure of Example 24 (a) to yield N-carbobenzyloxy-4-[(3-trifluoromethylphenyl)methylene]-L-proline. Hydrogenation of this material according to the procedure of Example 24 (b) yields cis-4-[(3-trifluoromethylphenyl)methyl]-L-proline.

(c) (4S)-1-[4-(Acetylthio)-1-oxobutyl]-4-[(3-trifluoromethylphenyl)methyl]-L-proline Reaction of cis-4-[(3-trifluoromethylphenyl)methyl]-L-proline with 4-acetylthiobutyroyl chloride according to the procedure of Example 24 (c) yields (4S)-1-[4-(acetylthio)-1-oxobutyl]-4-[(3-trifluoromethylphenyl)methyl]-L-proline.

(d) (4S)-1-(4-Mercapto-1-oxobutyl)-4-[(3-trifluoromethylphenyl)methyl]-L-proline Treatment of (4S)-1-[4-(acetylthio)-1-oxobutyl]-4-[(3-trifluoromethylphenyl)methyl]-L-proline with aqueous ammonia according to the procedure of Example 24 (d) yields (4S)-1-(4-mercapto-1-oxobutyl)-4-[(3-trifluoromethylphenyl)methyl]-L-proline.

EXAMPLE 31

(4S)-1-(3-Mercapto-1-oxopropyl)-4-(phenylethyl)-L-proline (a) (Phenylethyl)triphenylphosphonium chloride Treatment of triphenylphosphine with phenylethyl chloride according to the procedure of Example 25(a) yields (phenylethyl)triphenylphosphonium chloride.

(b) cis-4-(Phenylethyl)-L-proline (Phenylethyl)triphenylphosphonium chloride is reacted with sodium hydride in dimethylsulfoxide and then N-carbobenzyloxy-4-keto-L-proline, phenylmethyl ester to yield N-carbobenzyloxy-4-(phenylethylene)-L-proline, phenylmethyl ester. Hydrogenation of this material according to the procedure of Example 24(b) yields cis-4-(phenylethyl)-L-proline.

(c) (4S)-1-[3-(Acetylthio)-1-oxopropyl]-4-(phenylethyl)-L-proline

Reaction of cis-4-(phenylethyl)-L-proline with 3-acetylthiopropionyl chloride according to the procedure of Example 24 (c) yields (4S)-1-[3-(acetylthio)-1-oxopropyl]-4-(phenylethyl)-L-proline.

(d)

(4S)-1-(3-Mercapto-1-oxopropyl)-4-(phenylethyl)-L-proline

Treatment of (4S)-1-[3-(acetylthio)-1-oxopropyl]-4-(phenylethyl)-L-proline with aqueous ammonia according to the procedure of Example 24 (d) yields (4S)-1-(3-mercapto-1-oxopropyl)-4-(phenylethyl)-L-proline.

EXAMPLE 32

[1(S),4R]-1-(3-Mercapto-2-methyl-1-oxopropyl)-4-[(2-thienyl)methyl]-L-proline (a) [(2-Thienyl)methyl]triphenylphosphonium chloride Treatment of triphenylphosphine with 2-thienylmethyl chloride according to the procedure of Example 25 (a) yields [(2-thienyl)methyl]triphenylphosphonium chloride.

(b) cis-4-[(2-Thienyl)methyl]-L-proline

[(2-Thienyl)methyl]triphenylphosphonium chloride is reacted with sodium hydride in dimethylsulfoxide and then N-carbobenzyloxy-4-keto-L-proline according to the procedure of Example 24 (a) to yield N-carbobenzyloxy-4-[(2-thienyl)methylene]-L-proline. Hydrogenation of this material according to the procedure of Example 24 (b) yields cis-4-[(2-thienyl)methyl]-L-proline.

(c)

[1(S),4R]-1-[3-(Acetylthio)-2-methyl-1-oxopropyl]-4-[(2-thienyl)methyl]-L-proline Reaction of cis-4-[(2-thienyl)methyl]-L-proline with D-acetylthio-2-methylpropionyl chloride according to the procedure of Example 24 (c) yields [1(S),4R]-1-[3-(acetylthio)-2-methyl-1-oxopropyl]-4-[(2-thienyl)methyl]-L-proline.

(d)

[1(S),4R]-1-(3-Mercapto-2-methyl-1-oxopropyl)-4-[(2-thienyl)methyl]-L-proline

Treatment of [1(S),4R]-1-[3-(acetylthio)-2-methyl-1-oxopropyl]-4-[(2-thienyl)methyl]-L-proline with aqueous ammonia according to the procedure of Example 24 (d) yields [1(S),4R]-1-(3-mercapto-2-methyl-1-oxopropyl)-4-[(2-thienyl)methyl]-L-proline.

EXAMPLE 33

[1(S),4S]-1-(3-Mercapto-2-methyl-1-oxopropyl)-4-[(3-thienyl)methyl]-L-proline (a) [(3-Thienyl)methyl]triphenylphosphonium chloride Treatment of triphenylphosphine with 3-thienylmethyl chloride according to the procedure of Example 25 (a) yields [(3-thienyl)methyl]triphenylphosphonium chloride.

(b) cis-4-[(3-Thienyl)methyl]-L-proline

[(3-Thienyl)methyl]triphenylphosphonium chloride is reacted with sodium hydride in dimethylsulfoxide and then N-carbobenzyloxy-4-keto-L-proline according to the procedure of Example 24 (a) to yield N-carbobenzyloxy-4-[(3-thienyl)methylene]-L-proline. Hydrogenation of this material according to the procedure of Example 24 (b) yields cis-4-[(3-thienyl)methyl]-L-proline.

(c)

[1(S),4S]-1-[3-(Acetylthio)-2-methyl-1-oxopropyl]-4-[(3-thienyl)methyl]-L-proline Reaction of cis-4-[(3-thienyl)methyl]-L-proline with D-3-acetylthio-2-methylpropionyl chloride according to the procedure of Example 24 (c) yields [1(S),4S]-1-[3-(acetylthio)-2-methyl-1-oxopropyl]-4-[(3-thienyl)methyl]-L-proline.

(d)

[1(S),4S]-1-(3-Mercapto-2-methyl-1-oxopropyl)-4-[(3-thienyl)methyl]-L-proline

Treatment of [1(S),4S]-1-[3-(acetylthio)-2-methyl-1-oxopropyl]-4-[(3-thienyl)methyl]-L-proline with aqueous ammonia according to the procedure of Example 24 (d) yields [1(S),4S]-1-(3-mercapto-2-methyl-1-oxopropyl)-4-[(3-thienyl)methyl]-L-proline.

EXAMPLE 34

[1(S),4S]-1-(3-Mercapto-2-methyl-1-oxopropyl)-4-[(2-furyl)ethyl]-L-proline (a) [(2-Furyl)ethyl]triphenylphosphonium chloride Treatment of triphenylphosphine with 2-furylethyl chloride according to the procedure of Example 25(a) yields [(2-furyl)ethyl]triphenylphosphonium chloride.

(b) cis-4-[(2-Furyl)ethyl]-L-proline

[(2-Furyl)ethyl]triphenylphosphonium chloride is reacted with sodium hydride in dimethylsulfoxide and then N-carbobenzyloxy-4-keto-L-proline, phenylmethyl ester according to the procedure of Example 24(a) to yield N-carbobenzyloxy-4-[(2-furyl)ethylene]-L-proline, phenylmethyl ester. Hydrogenation of this material according to the procedure of Example 24(b) yields cis-4-[(2-furyl)ethyl]-L-proline.

(c)

[1(S),4S]-1-[3-(Acetylthio)-2-methyl-1-oxopropyl]-4-[(2-furyl)ethyl]-L-proline

Reaction of cis-4-[(2-furyl)ethyl]-L-proline with D-3-acetylthio-2-methylpropionyl chloride according to the procedure of Example 24 (c) yields [1(S),4S]-1-[3-(acetylthio)-2-methyl-1-oxopropyl]-4-[(2-furyl)ethyl]-L-proline.

(d)

[1(S),4S]-1-(3-Mercapto-2-methyl-1-oxopropyl)-4-[(2-furyl)ethyl]-L-proline

Treatment of [1(S),4S]-1-[3-(acetylthio)-2-methyl-1-oxopropyl]-4-[(2-furyl)ethyl]-L-proline with aqueous ammonia according to the procedure of Example 24 (d) yields [1(S),4S]-1-(3-mercapto-2-methyl-1-oxopropyl)-4-[(2-furyl)ethyl]-L-proline.

EXAMPLE 35

[1(S),4S]-1-(3-Mercapto-2-methyl-1-oxopropyl)-4-[(3-furyl)methyl]-L-proline (a) [(3-Furyl)methyl]triphenylphosphonium chloride Treatment of triphenylphosphine with 3-furylmethyl chloride according to the procedure of Example 25 (a) yields [(3-furyl)methyl]triphenylphosphonium chloride.

(b) cis-4-[(3-Furyl)methyl]-L-proline

[(3-Furyl)methyl]triphenylphosphonium chloride is reacted with sodium hydride in dimethylsulfoxide and then N-carbobenzyloxy-4-keto-L-proline according to the procedure of Example 24 (a) to yield N-carbobenzyloxy-4-[(3-furyl)methylene]-L-proline. Hydrogenation of this material according to the procedure of Example 24 (b) yields cis-4-[(3-furyl)methyl]-L-proline.

(c)

[1(S),4S]-1-[3-(Acetylthio)-2-methyl-1-oxopropyl]-4-[(3-furyl)methyl]-L-proline

Reaction of cis-4-[(3-furyl)methyl]-L-proline with D-3-acetylthio-2-methylpropionyl chloride according to the procedure of Example 24 (c) yields [1(S),4S]-1-[3-(acetylthio)-2-methyl-1-oxopropyl]-4-[(3-furyl)methyl]-L-proline.

(d)

[1(S),4S]-1-(3-Mercapto-2-methyl-1-oxopropyl)-4-[(3-furyl)methyl]-L-proline

Treatment of [1(S),4S]-1-[3-(acetylthio)-2-methyl-1-oxopropyl]-4-[(3-furyl)methyl]-L-proline with aqueous ammonia according to the procedure of Example 24 (d) yields [1(S),4S]-1-(3-mercapto-2-methyl-1-oxopropyl)-4-[(3-furyl)methyl]-L-proline.

EXAMPLE 36

[1(S),4S]-1-(3-Mercapto-2-methyl-1-oxopropyl)-4-[(4-pyridyl)methyl]-L-proline (a) [(4-Pyridyl)methyl]triphenylphosphonium chloride Treatment of triphenylphosphine with 4-pyridylmethyl chloride according to the procedure of Example 25 (a) yields [(4-pyridyl)methyl]triphenylphosphonium chloride.

(b) cis-4-[(4-Pyridyl)methyl]-L-proline

[(4-Pyridyl)methyl]triphenylphosphonium chloride is reacted with sodium hydride in dimethylsulfoxide and then N-carbobenzyloxy-4-keto-L-proline according to the procedure of Example 24 (a) to yield N-carbobenzyloxy-4-[(4-pyridyl)methylene]-L-proline. Hydrogenation of this material according to the procedure of Example 24 (b) yields cis-4-[(4-pyridyl)methyl]-L-proline.

(c)

[1(S),4S]-1-[3-(Acetylthio)-2-methyl-1-oxopropyl]-4-[(4-pyridyl)methyl]-L-proline Reaction of cis-4-[(4-pyridyl)methyl]-L-proline with D-3-acetylthio-2-methylpropionyl chloride according to the procedure of Example 24 (c) yields [1(S),4S]-1-[3-(acetylthio)-2-methyl-1-oxopropyl]-4-[(4-pyridyl)methyl]-L-proline.

(d)

[1(S),4S]-1-(3-Mercapto-2-methyl-1-oxopropyl)-4-[(4-pyridyl)methyl]-L-proline

Treatment of [1(S),4S]-1-[3-(acetylthio)-2-methyl-1-oxopropyl]-4-[(4-pyridyl)methyl]-L-proline with aqueous ammonia according to the procedure of Example 24 (d) yields [1(S),4S]-1-(3-mercapto-2-methyl-1-oxopropyl)-4-[(4-pyridyl)methyl]-L-proline.

EXAMPLE 37

[1(S),4S]-1-(3-Mercapto-2-methyl-1-oxopropyl)-4-[(cyclohexyl)methyl]-L-proline (a) [(Cyclohexyl)methyl]triphenylphosphonium chloride Treatment of triphenylphosphine with cyclohexylmethyl chloride according to the procedure of Example 25 (a) yields [(cyclohexyl)methyl]triphenylphosphonium chloride.

(b) cis-4-[(Cyclohexyl)methyl]-L-proline

[(Cyclohexyl)methyl]triphenylphosphonium chloride is reacted with sodium hydride in dimethylsulfoxide and then N-carbobenzyloxy-4-keto-L-proline according to the procedure of Example 24 (a) to yield N-carbobenzyloxy-4-[(cyclohexyl)methylene]-L-proline. Hydrogenation of this material according to the procedure of Example 24 (b) yields cis-4-[(cyclohexyl)methyl]-L-proline.

(c)

[1(S),4S]-1-[3-(Acetylthio)-2-methyl-1-oxopropyl]-4-[(cyclohexyl)methyl]-L-proline Reaction of cis-4-[(cyclohexyl)methyl]-L-proline with D-3-acetylthio-2-methylpropionyl chloride according to the procedure of Example 24 (c) yields [1(S),4S]-1-[3-(acetylthio)-2-methyl-1-oxopropyl]-4-[(cyclohexyl)methyl]-L-proline.

(d)

[1(S),4S]-1-(3-Mercapto-2-methyl-1-oxopropyl)-4-[(cyclohexyl)methyl]-L-proline

Treatment of [1(S),4S]-1-[3-(acetylthio)-2-methyl-1-oxopropyl]-4-[(cyclohexyl)methyl]-L-proline with aqueous ammona according to the procedure of Example 24 (d) yields [1(S),4S]-1-(3-mercapto-2-methyl-1-oxopropyl)-4-[(cyclohexyl)methyl]-L-proline.

EXAMPLE 38

[1(S),4S]-1-(3-Mercapto-2-trifluoromethyl-1-oxopropyl)-4-(phenylmethyl)-L-proline (a)

[1(S),4S]-1-[3-[[(4-Methoxy)phenylmethyl]thio]-2-trifluoromethyl-1-oxopropyl]-4-(phenylmethyl)-L-proline 3-[[(4-Methoxy)phenylmethyl]thio]-2-trifluoromethylpropionyl chloride is reacted with cis-4-(phenylmethyl)-L-proline to yield [1(S),4S]-1-[3-[[(4-methoxy)phenylmethyl]thio]-2-trifluoromethyl-1-oxopropyl]-4-(phenylmethyl)-L-proline.

(b)

[1(S),4S]-1-(3-Mercapto-2-trifluoromethyl-1-oxopropyl)-4-(phenylmethyl)-L-proline The [1(S),4S]-1-[3-[[(4-methoxy)phenylmethyl]thio]-2-trifluoromethyl-1-oxopropyl]-4-(phenylmethyl)-L-proline is mixed with trifluoroacetic acid and anisole under nitrogen. The solvents are removed under vacuum to yield as a residue [1(S),4]-1-(3-mercapto-2-trifluoromethyl-1-oxopropyl)-4-(phenylmethyl)-L-proline.

EXAMPLE 39

[1(S),4S]-4-[(4-Fluorophenyl)methyl]-1-(3-mercapto-2-methylthio-1-oxopropyl)-L-proline (a)

[1(S),4S]-4-[(4-Fluorophenyl)methyl]-1-[3-[[(4-methoxy)phenylmethyl]thio]-2-methylthio-1-oxopropyl]-L-proline 3-[[(4-Methoxy)phenylmethyl]thio]-2-methylthiopropionyl chloride is reacted with cis-4-[(4-fluorophenyl)methyl]-L-proline to yield [1(S),4S]-4-[(4-fluorophenyl)methyl]-1-[3-[[(4-methoxy)phenylmethyl]thio]-2-methylthio-1-oxopropyl]-L-proline.

(b)

[1(S),4S]-4-[(4-Fluorophenyl)methyl]-1-(3-mercapto-2-methylthio-1-oxopropyl)-L-proline The [1(S),4S]-4-[(4-fluorophenyl)methyl]-1-[3-[[(4-methoxy)phenylmethyl]thio]-2-methylthio-1-oxopropyl]-L-proline is mixed with trifluoroacetic acid and anisole under nitrogen. The solvents are removed under vacuum to yield as a residue [1(S),4S]-4-[(4-fluorophenyl)methyl]-1-(3-mercapto-2-methylthio-1-oxopropyl)-L-proline.

EXAMPLE 40

[1(S),4S]-4-[(4-Chlorophenyl)methyl]-1-(3-mercapto-2-methyl-1-oxopropyl)-L-proline (a) [(4-Chlorophenyl)methyl]triphenylphosphonium chloride Triphenylphosphine (158 g., 0.60 mole) and 97 g. of 4-chlorobenzyl chloride are reacted in 800 ml. of boiling xylene according to the procedure of Example 25 (a) to yield 161 g. of colorless solid [(4-chlorophenyl)methyl]triphenylphosphonium chloride; m.p. 283°–285°.

(b)

N-Carbobenzyloxy-4-[(4-chlorophenyl)methylene]-L-proline

Interaction of 15.2 g. (0.32 mole) of 50% sodium hydride (oil dispersion) with 300 ml. of dimethyl sulfoxide, followed by treatment with a suspension of 135 g. (0.32 mole) of [(4-chlorophenyl)methyl]triphenylphosphonium chloride in 300 ml. of dimethyl sulfoxide (warmed to 70° and then cooled to 22°) and then with a solution of 26.4 g. (0.1 mole) of N-carbobenzyloxy-4-keto-L-proline in 80 ml. of dimethyl sulfoxide according to the procedure of Example 24 (a) gives 13 g. of pale yellow product as a sticky foam. This material is dissolved in 30 ml. of acetonitrile and treated with 6.5 g. of dicyclohexylamine to yield 15.3 g. of nearly colorless N-carbobenzyloxy-4-[(4-chlorophenyl)methylene]-L-proline, dicyclohexylamine salt; m.p. 180°–182° (s. 177°); $[\alpha]_D^{25} +6.2°$ (c, 1% in chloroform).

Anal. Cal'd. for $C_{20}H_{18}ClNO_4 \cdot C_{12}H_{23}N$: C, 69.48; H, 7.47; N, 5.07; Cl, 6.41; Found: C, 69.14; H, 7.20; N, 5.03; Cl, 6.23.

The above dicyclohexylamine salt (7.5 g.) is suspended in ethyl acetate and treated with 10% potassium bisulfate according to the procedure of Example 24(a) to give 5.3 g. of sticky N-carbobenzyloxy-4-[(4-chlorophenyl)methylene]-L-proline.

(c) cis-4-[(4-Chlorophenyl)methyl]-L-proline, hydrobromide

A solution of 5.3 g. (0.014 mole) of N-carbobenzyloxy-4-[(4-chlorophenyl)methylene]-L-proline in 150 ml. of ethanol is treated with 0.45 g. of platinum dioxide and shaken on a Parr hydrogenator at a starting pressure of 15 lbs. (bottle guage). The uptake of hydrogen is carefully monitored and whenever the pressure falls to 5 lbs the bottle is replenished with hydrogen to 15 lbs. A noticeable slowing down of the rate of hydrogen uptake is observed after eight minutes and the hydrogenation is interrupted after a total of ten minutes (21.5 lbs. of hydrogen). The catalyst is filtered off (celite bed under nitrogen atmosphere), washed well with ethanol, and the combined filtrates are evaporated, finally at 0.2 mm., to yield 4.6 g. of N-carbobenzyloxy-cis-4-[(4-chlorophenyl)methyl]-L-proline as a colorless brittle foam.

This material (4.5 g., 0.012 mole) is treated with 25 ml. of hydrogen bromide in acetic acid (30–32%), stoppered loosely, and stirred magnetically. After 30 minutes the yellow-orange mixture (some crystalline product separates) is diluted to 500 ml. with ether to complete precipitation and stirred with cooling for 30 minutes. The light pink product is filtered under nitrogen, washed with ether, and dried in vacuo to yield 3.3 g. of cis-4-[(4-chlorophenyl)methyl]-L-proline, hydrobromide; m.p. 233°–235° (dec., preceded by gradual darkening and sintering); $[\alpha]_D^{25} +1.5°$. (c, 1% in methanol).

Anal. Calc'd. for $C_{12}H_{14}ClNO_2 \cdot HBr$: C, 44.95; H, 4.72; N, 4.37; Br, 24.92; Found: C, 45.03; H, 4.72; N, 4.38; Br, 24.65.

(d)

[1(S),4S]-1-[3-(Acetylthio)-2-methyl-1-oxopropyl]-4-[(4-chlorophenyl)methyl]-L-proline Interaction of cis-4-[(4-chlorophenyl)methyl]-L-proline, hydrobromide (3.3 g.; 0.10 mole) and 2.1 g. (0.0116 mole) of D-3-acetylthio-2-methylpropionyl chloride in 35 ml. of water in the presence of sodium carbonate according to the procedure of Example 24(c) gives 4.0 g. of pale pink glass-like product. The latter is dissolved in 30 ml. of ethyl acetate and treated with 2.0 g. of dicyclohexylamine to yield 4.25 g. of crude dicyclohexylamine salt; m.p. 188°–190° (s. 181°); $[\alpha]_D^{25} -67°$ (c, 1% in ethanol). Crystallization from 100 ml. of acetonitrile yields 3.6 g. of [1(S),4S]-1-[3-(acetylthio)-2-methyl-1-oxopropyl]-4-[(4-chlorophenyl)methyl]-L-proline, dicyclohexylamine salt; 189°–191° (s. 181°); $[\alpha]_D^{25} -68°$ (c, 1% in ethanol).

Anal. Calc'd. for $C_{18}H_{22}ClNO_4S \cdot C_{12}H_{23}N$: C, 63.75; H, 8.02; N, 4.96; Cl, 6.27; S, 5.67; Found: C, 63.75; H, 7.94; N, 4.93; Cl, 6.28; S, 5.43.

This purified dicyclohexylamine salt (3.5 g.) is converted to the free acid by suspending in ethyl acetate and treating with 10% potassium bisulfate according to the procedure of Example 24 (c) to yield 2.5 g. of [1(S),4S]-1-[3-(acetylthio)-2-methyl-1-oxopropyl]-4-[(4-chlorophenyl)methyl]-L-proline as a sticky foam; $[\alpha]_D^{25} -107°$ (c, 1% in ethanol). $R_f$ 0.54 (90:5:5, methylene chloride:methanol:acetic acid on silica gel; visualized with phosphomolybdic acid plus heat).

(e)

[1(S),4S]-4-[(4-Chlorophenyl)methyl]-1-(3-mercapto-2-methyl-1-oxopropyl)-L-proline Treatment of [1(S),4S]-1-[3-(acetylthio)-2-methyl-1-oxopropyl]-4-[(4-chlorophenyl)methyl]-L-proline (2.4 g., 0.0062 mole) with 4.5 ml. of concentrated ammonia hydroxide in 11 ml. of water according to the procedure of Example 2 gives 1.95 g. of [1(S),4S]-4-[(chloro-phenyl)methyl]-1-(3-mercapto-2-methyl-1-oxopropyl)-L-proline as a colorless amorphous solid; m.p. 50°–53° (s. ~43°); [α]$_D^{25}$ −74° (c, 1% in ethanol). R$_f$ 0.46 (90:5:5 methylene chloride:methanol:acetic acid on silica gel; visualized with phosphomolybdic acid plus heat).

Anal. Calc'd. for $C_{16}H_{20}ClNO_3S.0.25H_2O$: C, 55.48; H, 5.96; N, 4.04; Cl, 10.24; S, 9.26; Found: C, 55.48; H, 6.02; N, 4.27; Cl. 10.39; S, 9.19.

Treatment of this material with 1-adamantanamine in ethyl acetate yields [1(S),4S]-4-[(4-chlorophenyl)methyl]-1-(3-mercapto-2-methyl-1-oxopropyl)-L-proline, 1-adamantanamine salt; m.p. 218°–220° (dec.) (s. 214°).

EXAMPLE 41

[1(S),4R]-1-(3-Mercapto-2-methyl-1-oxopropyl)-4-phenyl, L-proline, sodium salt

An aqueous solution of the product from Example 2 is treated with a slight excess of sodium bicarbonate. The solution is lyophilized to yield [1(S),4R]-1-(3-mercapto-2-methyl-1-oxopropyl)-4-phenyl-L-proline, sodium salt.

EXAMPLE 42

[1(S),4S]-1-(3-Mercapto-2-methyl-1-oxopropyl)-4-(phenylmethyl)-L-proline, sodium salt An aqueous solution of the product from Example 24 is treated with a slight excess of sodium bicarbonate. The solution is lyophilized to yield [1(S),4S]-1-(3-mercapto-2-methyl-1-oxopropyl)-4-(phenylmethyl)-L-proline, sodium salt.

EXAMPLE 43

[1(S),1'(S),4R,4'R]-1,1'-[Dithiobis(2-methyl-1-oxopropane-3,1-diyl)]bis[4-phenyl-L-proline]

A solution of the product from Example 2 is dissolved in ethanol, stirred and treated with a solution of one equivalent of iodine in ethanol. The pH of the solution is maintained at 6–7 by the addition of N-sodium hydroxide solution. The solvent is evaporated and the residue extracted with ethyl acetate. After drying over MgSO$_4$, the solution is filtered and the solvent evaporated to give [1(S),1'(S),4R,4'R]-1,1'-[dithiobis(2-methyl-1-oxopropane-3,1-diyl)]bis[4-phenyl-L-proline].

EXAMPLE 44

[1(S),1'(S),4S,4'S]-1,1'-[Dithiobis(2-methyl-1-oxopropane-3,1-diyl)]bis[(4-phenylmethyl)-L-proline]

A solution of the product from Example 24 is dissolved in ethanol, stirred and treated with a solution of one equivalent of iodine in ethanol. The pH of the solution is maintained at 6–7 by the addition of N-sodium hydroxide solution. The solvent is evaporated and the residue extracted with ethyl acetate. After drying over MgSO$_4$, the solution is filtered and the solvent evaporated to give [1(S),1'(S),4S,4'S]-1,1'-[dithiobis(2-methyl-1-oxopropane-3,1-diyl)]bis[(4-phenylmethyl)-L-proline].

EXAMPLE 45

[1(S),4R]-1-[3-(Acetylthio)-2-methyl-1-oxopropyl]-4-phenyl-L-proline, methyl ester A solution of the product from Example 1 in ether is treated with a slight excess of diazomethane. After standing at room temperature, the solvent is evaporated to give [1(S),4R]-1-[3-(acetylthio)-2-methyl-1-oxopropyl]-4-phenyl-L-proline, methyl ester.

EXAMPLE 46

[1(S),4R]-1-(3-Mercapto-2-methyl-1-oxopropyl)-4-phenyl-L-proline, methyl ester

The methyl ester product from Example 45 is treated with concentrated ammonia according to the procedure of Example 2 to give [1(S),4R]-1-(3-mercapto-2-methyl-1-oxopropyl)-4-phenyl-L-proline, methyl ester.

EXAMPLE 47

1000 tablets each containing the following ingredients

| | | |
|---|---:|---|
| [1(S),4S]-1-(3-Mercapto-2-methyl-1-oxopropyl)-4-(phenylmethyl)-L-proline | 100 | mg. |
| Corn starch | 50 | mg. |
| Gelatin | 7.5 | mg. |
| Avicel (microcrystalline cellulose) | 25 | mg. |
| Magnesium stearate | 2.5 | mg. |
| | 185 | mg. | are prepared (from sufficient bulk quantities) by mixing the [1(S),4S]-1-(3-mercapto-2-methyl-1-oxopropyl)-4-(phenylmethyl)-L-proline and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner tablets containing 100 mg. of the product of any of Examples 1 to 23 and 25 to 46 can be prepared.

EXAMPLE 48

1000 tablets each containing the following ingredients:

| | | |
|---|---:|---|
| [1(S),4S]-1-(3-Mercapto-2-methyl-1-oxopropyl)-4-[(4-fluorophenyl)methyl]-L-proline | 50 | mg. |
| Lactose | 25 | mg. |
| Avicel | 38 | mg. |
| Cornstarch | 15 | mg. |
| Magnesium stearate | 2 | mg. |
| | 130 | mg. | are prepared by admixing the [1(S),4S]-1-(3-mercapto-2-methyl-1-oxopropyl)-4-[(4-fluorophenyl)methyl]-L-proline, lactose and Avicel and then blending with the corn starch. Magnesium stearate is added. The dry mixture is compressed in a tablet press to form 1000 130 mg. tablets each containing 50 mg. of active ingredient. The tablets are coated with a solution of Methocel E 15 (methyl cellulose) including as a color a lake containing yellow #6.

In a similar manner tablets containing 50 mg. of the product of any of Examples 1 to 24 and 26 to 46 can be prepared.

EXAMPLE 49

Two piece #1 gelatin capsules each containing 100 mg. of [1(S),4R]-1-(3-mercapto-2-methyl-1-oxopropyl)-4-phenyl-L-proline, sodium salt, are filled with a mixture of the following ingredients:

| | | |
|---|---:|---|
| [1(S),4R]-1-(3-Mercapto-2 methyl-1-oxopropyl)-4-phenyl-L-proline, sodium salt | 100 | mg. |
| Magnesium stearate | 7 | mg. |
| Lactose | 193 | mg. |

In a similar manner capsules containing 100 mg. of the product of any of Examples 1 to 40 or 42 to 46 can be prepared.

EXAMPLE 50

An injectable solution is prepared as follows:

| | | |
|---|---:|---|
| [1(S),4R]-4-Cyclohexyl-1-(3-mercapto-2-methyl-1-oxopropyl)-L-proline | 500 | g. |
| Methyl paraben | 5 | g. |
| Propyl paraben | 1 | g. |
| Sodium chloride | 25 | g. |
| Water for injection qs. | 5 | l |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

In a similar manner an injectable solution containing 100 mg. of active ingredients per ml. of solution can be prepared for the product of any of Example 1 to 6 and 8 to 46.

EXAMPLE 51

1000 tablets each containing the following ingredients:

| | | |
|---|---:|---|
| [1(S),4S]-1-(3-Mercapto-2-methyl-1-oxopropyl)-4-(phenylmethyl)-L-proline | 100 | mg. |
| Avicel (Microcrystalline cellulose) | 100 | mg. |
| Hydrochlorothiazide | 12.5 | mg. |
| Lactose U.S.P. | 113 | mg. |
| Corn starch U.S.P. | 17.5 | mg. |
| Stearic acid U.S.P. | 7 | mg. |
| | 350 | mg. | are produced from sufficient bulk quantities by slugging the [1(S),4S]-1-(3-mercapto-2-methyl-1-oxopropyl)-4-(phenylmethyl)-L-proline, Avicel and a portion of the stearic acid. The slugs are ground and passed through a #2 screen, then mixed with the hydrochlorothiazide, lactose, corn starch and remainder of the stearic acid. The mixture is compressed into 350 mg. capsule shaped tablets in a tablet press. The tablets are scored for dividing in half.

In a similar manner tablets can be prepared containing 100 mg. of the product of any of Examples 1 to 23 and 25 to 46.

What is claimed is:
1. A compound of the formula

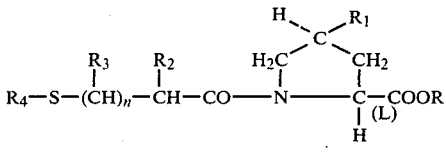

including a salt thereof wherein
R is hydrogen or lower alkyl;
R$_1$ is —(CH$_2$)$_m$-cycloalkyl wherein cycloalkyl is a saturated ring of 3 to 7 carbons, 1-cyclohexenyl, 1,4-cyclohexadienyl,

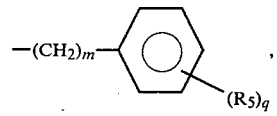

—(CH$_2$)$_m$-(α-naphthyl), —(CH$_2$)$_m$-(β-naphthyl),

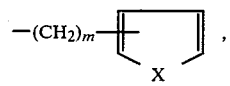

or

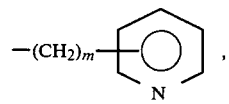

R$_2$ and R$_3$ are independently selected from the group consisting of hydrogen, lower alkyl, lower alkylthio, and halo substituted lower alkyl;
n is zero, one or two;
R$_4$ is hydrogen,

p-methoxybenzyloxycarbonyl, t-butoxycarbonyl, or

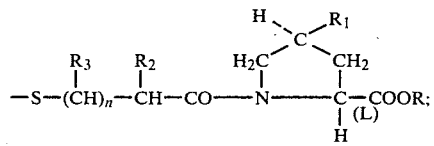

m is zero, one, two or three;
R$_5$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenyloxy, phenylthio, or phenylmethyl;
q is one, two or three provided that q is more than one only if R$_5$ is hydrogen, methyl, methoxy, chloro, or fluoro;
R$_6$ is lower alkyl, halo substituted lower alkyl, —(CH$_2$)$_m$-cycloalkyl wherein cycloalkyl is a saturated ring of 3 to 7 carbons,

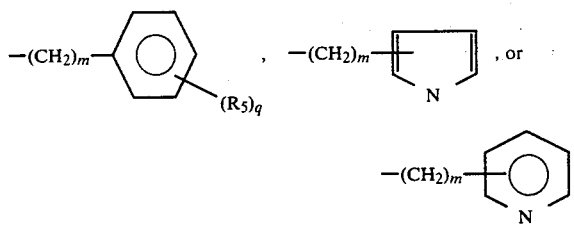

wherein m, q, and R₅ are as defined above; and
X is oxygen or sulfur.

2. The compound of claim 1 wherein R is hydrogen; R₂ is hydrogen, methyl, trifluoromethyl, or methylthio; R₃ is hydrogen; n is zero or one; and R₄ is hydrogen, acetyl, or benzoyl.

3. The compound of claim 2 wherein R₁ is cyclohexyl or

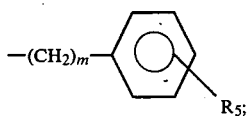

m is zero, one or two; and R₅ is hydrogen, methyl, methoxy, methylthio, chloro, fluoro, trifluoromethyl, or hydroxy.

4. The compound of claim 3 wherein R₁ is cyclohexyl.

5. The compound of claim 4 wherein R₂ is methyl; n is one; and R₄ is hydrogen.

6. The compound of claim 5, [1(S),4R]-4-cyclohexyl-1-(3-mercapto-2-methyl-1-oxopropyl)-L-proline.

7. The compound of claim 3 wherein R₁ is

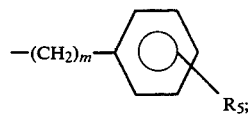

m is zero, one or two; and R₅ is hydrogen, methyl, methoxy, methylthio, chloro, fluoro, trifluoromethyl or hydroxy.

8. The compound of claim 7 wherein R₁ is phenyl.

9. The compound of claim 8 wherein R₂ is methyl; n is one; and R₄ is acetyl.

10. The compound of claim 8 wherein R₂ is methyl; n is one; and R₄ is hydrogen.

11. The compound of claim 10, [1(S),4R]-1-(3-mercapto-2-methyl-1-oxopropyl)-4-phenyl-L-proline.

12. The compound of claim 7 wherein R₁ is phenylmethyl.

13. The compound of claim 12 wherein R₂ is methyl; n is one; and R₄ is acetyl.

14. The compound of claim 12 wherein R₂ is methyl; n is one; and R₄ is hydrogen.

15. The compound of claim 14, [1(S),4S]-1-(3-mercapto-2-methyl-1-oxopropyl)-4-(phenylmethyl)-L-proline.

16. The compound of claim 7 wherein R₁ is (4-fluorophenyl)methyl.

17. The compound of claim 16 wherein R₂ is methyl; n is one; and R₄ is acetyl.

18. The compound of claim 16 wherein R₂ is methyl; n is one; and R₄ is hydrogen.

19. The compound of claim 18, [1(S),4S]-4-[(4-fluorophenyl)methyl]-1-(3-mercapto-2-methyl-1-oxopropyl)-L-proline, L-arginine salt.

20. The compound of claim 7 wherein R₁ is (4-chlorophenyl)methyl.

21. The compound of claim 20 wherein R₂ is methyl; n is one; and R₄ is acetyl.

22. The compound of claim 20 wherein R₂ is methyl; n is one; and R₄ is hydrogen.

23. The compound of claim 22, [1(S),4S]-4-[(4-chlorophenyl)methyl]-1-(3-mercapto-2-methyl-1-oxopropyl)-L-proline.

24. The compound of claim 7 wherein R₁ is phenylethyl.

25. The compound of claim 24 wherein R₂ is methyl; n is one; and R₄ is acetyl.

26. The compound of claim 24 wherein R₂ is methyl; n is one; and R₄ is hydrogen.

27. The compound of claim 26, [1(S),4S]-1-(3-mercapto-2-methyl-1-oxopropyl)-4-(phenylethyl)-L-proline.

28. A compound of the formula

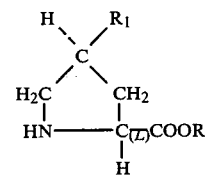

wherein
R is hydrogen or lower alkyl;
R₁ is —(CH₂)$_m$-cycloalkyl wherein cycloalkyl is a saturated ring of 3 to 7 carbons, 1-cyclohexenyl, 1,4-cyclohexadienyl,

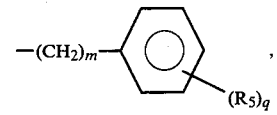

—(CH₂)$_m$-(α-naphthyl), —(CH₂)$_m$-(β-naphthyl),

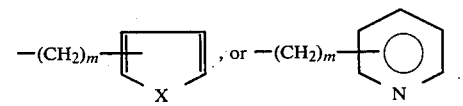

m is zero, one, two or three;
R₅ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenyloxy, phenylthio, or phenylmethyl;
q is one, two or three provided that q is more than one only if R₅ is hydrogen, methyl, methoxy, chloro, or fluoro; and
X is oxygen or sulfur.

29. The compound of claim 28 wherein R₁ is cyclohexyl or

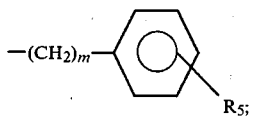

m is zero, one or two; and $R_5$ is hydrogen, methyl, methoxy, methylthio, chloro, fluoro, trifluoromethyl or hydroxy.

30. The compound of claim 29 wherein $R_1$ is cyclohexyl.

31. The compound of claim 29 wherein $R_1$ is phenyl.

32. The compound of claim 29 wherein $R_1$ is phenylmethyl.

33. The compound of claim 29 wherein $R_1$ is (4-fluorophenyl)methyl.

34. The compound of claim 29 wherein $R_1$ is (4-chlorophenyl)methyl.

35. A composition useful for treating hypertension comprising a pharmaceutically acceptable carrier and an effective amount of a hypotensive agent of the formula

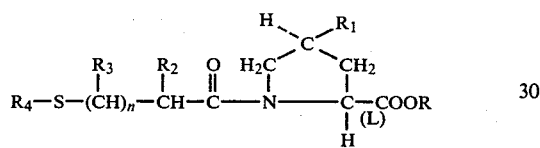

including a pharmaceutically acceptable salt thereof wherein

R is hydrogen or lower alkyl;

$R_1$ is $(CH_2)_m$-cycloalkyl wherein cycloalkyl is a saturated ring of 3 to 7 carbons, 1-cyclohexenyl, 1,4-cyclohexadienyl,

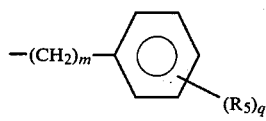

$-(CH_2)_m$-($\alpha$-naphthyl), $-(CH_2)_m$-($\beta$-naphthyl),

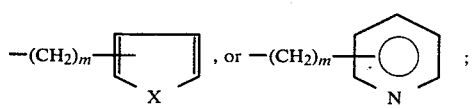

$R_2$ and $R_3$ are independently selected from the group consisting of hydrogen, lower alkyl, lower alkylthio, and halo substituted lower alkyl;

$R_4$ is hydrogen,

or

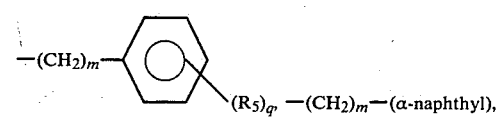

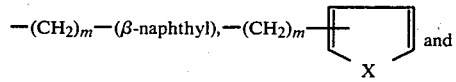

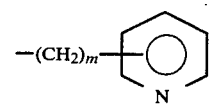

$R_5$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenyloxy, phenylthio or phenylmethyl;

m is zero, one, two or three;

q is one, two or three provided that q is more than one only if $R_5$ is hydrogen, methyl, methoxy, chloro or fluoro;

$R_6$ is lower alkyl of 1 to 6 carbons, halo substituted lower alkyl of 1 to 6 carbons, $-(CH_2)_m$-cycloalkyl wherein cycloalkyl is as defined above,

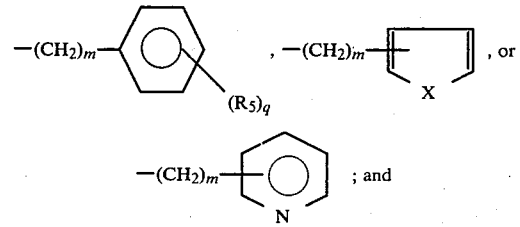

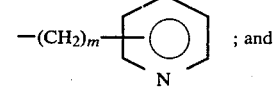

X is oxygen or sulfur.

36. The composition of claim 35 also including a diuretic.

37. The method of alleviating hypertension which comprises administering an effective amount of the composition of claim 35.

* * * * *